United States Patent [19]

Kawauchi et al.

[11] Patent Number: 5,739,012
[45] Date of Patent: Apr. 14, 1998

[54] TISSUE PLASMINOGEN ACTIVATOR AND PROCESS OF PREPARATION

[75] Inventors: Yasushi Kawauchi, Tokyo; Toshiyuki Takemoto, Saitama; Makoto Takayama; Masami Yokota, both of Tokyo; Masao Kato; Kimio Katsuta, both of Saitama, all of Japan

[73] Assignee: Yamanouchi Pharmaceutical Co., Ltd., Tokyo, Japan

[21] Appl. No.: 712,999

[22] Filed: Sep. 10, 1996

Related U.S. Application Data

[62] Division of Ser. No. 237,249, May 4, 1994, Pat. No. 5,556,621, which is a continuation of Ser. No. 810,561, Dec. 20, 1991, abandoned, which is a continuation of Ser. No. 474,113, Apr. 27, 1990, abandoned.

[30] Foreign Application Priority Data

| | | | |
|---|---|---|---|
| Oct. 29, 1987 | [JP] | Japan | 62-274770 |
| Dec. 18, 1987 | [JP] | Japan | 62-320785 |
| Mar. 23, 1988 | [JP] | Japan | 63-70126 |
| Jul. 27, 1988 | [JP] | Japan | 63-189351 |

[51] Int. Cl.$^6$ .............. C12P 21/02; C12N 1/21; C12N 5/10; C07H 21/04
[52] U.S. Cl. .............. 435/69.6; 435/69.1; 435/252.3; 435/325; 536/23.5
[58] Field of Search .............. 435/69.6, 69.1, 435/252.3, 325; 536/23.5

[56] References Cited

U.S. PATENT DOCUMENTS 5,037,646  8/1991  Higgins et al. .............. 435/94.64

*Primary Examiner*—Robert A. Wax
*Assistant Examiner*—Kowai Lau
*Attorney, Agent, or Firm*—Burgess, Ryan & Wayne

[57] ABSTRACT

The present invention relates to improved plasminogen activators (improved t-PA) which have a prolonged biological half life, an increased stability to heat and acids and can be expected to be effective as inhibiting inflammation around the site in which thrombus is formed.

4 Claims, 27 Drawing Sheets

1. 71MER 5' GATCTATGGATGCAATGAAGAGAG
GGCTCTGCTGTGTGCTGCTACTCT
GCGGAGCAGTCTTCGTTTCGCCC 3'
2. 48MER 5' AGCCAGGAAATCCATGCCCGATTC
AGAAGAGGAGCCAGGTCTTACCAA 3'
3. 55MER 5' GACTGCTCCGCAGAGTAGCAGCAC
ACAGCAGAGCCCTCTCTTCATTGC
ATCCATA 3'
4. 644MER 5' TCACTTGGTAAGACCTGGCTCCTC
TTCTGAATCGGGCATGGATTTCCT
GGCTGGGCGAAACGAA 3'
5. 67MER 5' GTGATCTGCAGAGATGAAAAAACG
CAGATGATATACCAGCAACATCAG
TCATGGCTGCGCCCTGTGC 3'
6. 61MER 5' TCAGAAGCAACCGGGTGGAATATT
GCTGGTGCAACAGTGGCAGGGCAC
AGTGCCACTCAGT 3'
7. 53MER 5' GCCTGTCAAAAGTTGCAGCGAGCC
AAGGTGTTTCAACGGGGGCACCTG
CCAGC 3'
7'. 54MER 5' GCCTGTCAAAAGTTGCAGCGAGCC
AAGGTGTTTCAACGGGGGCACCTG
CCAGGA 3'
8. 51MER 5' GCCATGACTGATGTTGGTGGTATA
TCATCTGCGTTTTTTCATCTCT
GC
AGA 3'

*FIG. 1A*

9. 61MER 5' TGTGCCCTGCCACTGTTGCACCAG
CAATATTCCACCCGGTTGCTTCTG
AGCACAGGGCGCA 3'
10. 70MER 5' AGCTTGCTGGCAGGTGCCCCCGTT
GAAACACCTTGGCTCGCTGCAACT
TTTGACAGGCACTGAGTGGCAC 3'
11. 68MER 5' AAGCTTTGTACTTCTCAGATTTCG
TGTGCCAGTGCCCCGAAGGATTTG
CTGGGAAGTGCTGTGAAATA 3'
11'. 67MER 5' AGCTTTGTACTTCTCAGATTTCGT
GTGCCAGTGCCCCGAAGGATTTGC
TGGGAAGTGCTGTGAAATA 3'
12. 49MER 5' GATACTCGAGCCACGTCTGAGGGA
AACAGTGACTGCTACTTTGGGAAT
G 3'
13. 59MER 5' GGTCAGCCTACCGTGGTACCCACA
GCCTCACCGAGTCGGGTGCCTCCT
GCCTCCCATGG 3'
14. 50MER 5' TTCCAGCAAATCCTTCGGGGCAC
TGGCACACGAAATCTGAGAAGTAC
AA 3'
15. 74MER 5' GGTAGGCTGACCCATTCCCAAAGT
AGCAGTCACTGTTTCCCTCAGACG
TGGCTCGAGTATCTATTTCACAGC
AC 3'
16. 51MER 5' AATTCCATGGGAGGCAGGAGGCAC
CCGACTCGGTGAGGCTGTGGGTAC
CAC 3'

*FIG. 1B*

```
 5'  GATCTATGGATGCAATGAAGAGAGGGCTCT
     ATACCTACGTTACTTCTCTCCCGAGA
     GCTGTGTGCTGCTACTCTGCGGAGCAGTCT
 5   CGACACGACGATGAGACGCCTCGTCAGA
     TCGTTTCGCCCAGCCAGGAAATCCATGCCC
     AGCAAAGCGGGTCGGTCCTTTAGGTACGGG
     GATTCAGAAGAGGAGCCAGGTCTTACCAAG
     CTAAGTCTTCTCCTCGGTCCAGAATGGTTC
10   TGATCTGCAGAGATGAAAAACGCAGATGA
     ACTAGACGTCTCTACTTTTTGCGTCTACT
     TATACCAGCAACATCAGTCATGGCTGCGCC
     ATATGGTCGTTGTAGTCAGTACCGACGCGG
     CTGTGCTCAGAAGCAACCGGGTGGAATATT
15   GACACGAGTCTTCGTTGGCCCACCTTATAA
     GCTGGTGCAACAGTGGCAGGGCACAGTGCC
     CGACCACGTTGTCACCGTCCCGTGTCACGG
     ACTCAGTGCCTGTCAAAAGTTGCAGCGAGC
     TGAGTCACGGACAGTTTTCAACGTCGCTCG
20   CAAGGTGTTTCAACGGGGGCACCTGCCAGC
     GTTCCACAAAGTTGCCCCGTGGACGGTCG
     AAGCTTTGTACTTCTCAGATTTCGTGTGCC
     TTCGAAACATGAAGAGTCTAAAGCACACGG
     AGTGCCCCGAAGGATTTGCTGGGAAGTGCT
25   TCACGGGGCTTCCTAAACGACCCTTCACGA
     GTGAAATAGATACTCGAGCCACGTCTGAGG
     CACTTTATCTATGAGCTCGGTGCAGACTCC
```

*FIG. 2A*

```
GAAACAGTGACTGCTACTTTGGGAATGGGT
CTTTGTCACTGACGATGAAACCCTTACCCA
CAGCCTACCGTGGTACCCACAGCCTCACCG
GTCGGATGGCACCATGGGTGTCGGAGTGGC
AGTCGGGTGCCTCCTGCCTCCCATGG    3'
TCAGCCCACGGAGGACGGAGGGTACCTTAA5'
```

*FIG. 2B*

```
5' ATGGATGCAATGAAGAGAGGGCTCTGCTGT
   GTGCTGCTACTCTGCGGAGCAGTCTTCGTT
   TCGCCCAGCCAGGAAATCCATGCCCGATTC
 5 AGAAGAGGAGCCAGGTCTTACCAAGTGATC
   TGCAGAGATGAAAAAACGCAGATGATATAC
   CAGCAACATCAGTCATGGCTGCGCCCTGTG
   CTCAGAAGCAACCGGGTGGAATATTGCTGG
   TGCAACAGTGGCAGGGCACAGTGCCACTCA
10 GTGCCTGTCAAAAGTTGCAGCGAGCCAAGG
   TGTTTCAACGGGGGCACCTGCCAGCAAGCT
   TTGTACTTCTCAGATTTCGTGTGCCAGTGC
   CCCGAAGGATTTGCTGGGAAGTGCTGTGAA
   ATAGATACTCGAGCCACGTCTGAGGGAAAC
15 AGTGACTGCTACTTTGGGAATGGGTCAGCC
   TACCGTGGTACCCACAGCCTCACCGAGTCG
   GGTGCCTCCTGCCTCCCATGGAATTCCATG
   ATCCTGATAGGCAAGGTTTACACAGCACAG
   AACCCCAGTGCCCAGGCACTGGGCCTGGGC
20 AAACATAATTACTGCCGGAATCCTGATGGG
```

*FIG. 5A*

```
GATGCCAAGCCCTGGTGCCACGTGCTGAAG
AACCGCAGGCTGACGTGGGAGTACTGTGAT
GTGCCCTCCTGCTCCACCTGCGGCCTGAGA
CAGTACAGCCAGCCTCAGTTTCGCATCAAA
GGAGGGCTCTTCGCCGACATCGCCTCCCAC
CCCTGGCAGGCTGCCATCTTTGCCAAGCAC
AGGAGGTCGCCCGGAGAGCGGTTCCTGTGC
GGGGGCATACTCATCAGCTCCTGCTGGATT
CTCTCTGCCGCCCACTGCTTCCAGGAGAGG
TTTCCGCCCCACCACCTGACGGTGATCTTG
GGCAGAACATACCGGGTGGTCCCTGGCGAG
GAGGAGCAGAAATTTGAAGTCGAAAAATAC
ATTGTCCATAAGGAATTCGATGATGACACT
TACGACAATGACATTGCGCTGCTGCAGCTG
AAATCGGATTCGTCCCGCTGTGCCCAGGAG
AGCAGCGTGGTCCGCACTGTGTGCCTTCCC
CCGGCGGACCTGCAGCTGCCGGACTGGACG
GAGTGTGAGCTCCGGCTACGGCAAGCAT
GAGGCCTTGTCTCCTTTCTATTCGGAGCGG
CTGAAGGAGGCTCATGTCAGACTGTACCCA
TCCAGCCGCTGCACATCACAACATTTACTT
AACAGAACAGTCACCGACAACATGCTGTGT
```

FIG. 5B

```
GCTGGAGACACTCGGAGCGGCGGGCCCCAG
GCAAACTTGCACGACGCCTGCCAGGGCGAT
TCGGGAGGCCCCCTGGTGTGTCTGAACGAT
GGCCGCATGACTTTGGTGGGCATCATCAGC
TGGGGCCTGGGCTGTGGACAGAAGGATGTC
CCGGGTGTGTACACCAAGGTTACCAACTAC
CTAGACTGGATTCGTGACAACATGCGACCG
TGA 3'
```
[wherein A is deoxyadenyl, G is deoxyguanyl,
C is deoxycytidyl and T is deoxythymidyl]

*FIG. 5C*

```
5' ATGGATGCAATGAAGAGAGGGCTCTGCTGT
   GTGCTGCTACTCTGCGGAGCAGTCTTCGTT
   TCGCCCAGCCAGGAAATCCATGCCCGATTC
 5 AGAAGAGGAGCCAGGTCTTACCAAGTGATC
   TGCAGAGATGAAAAAACGCAGATGATATAC
   CAGCAACATCAGTCATGGCTGCGCCCTGTG
   CTCAGAAGCAACCGGGTGGAATATTGCTGG
   TGCAACAGTGGCAGGGCACAGTGCCACTCA
10 GTGCCTGTCAAAAGTTGCAGCGAGCCAAGG
   TGTTTCAACGGGGGCACCTGCCAGCAAGCT
   TTGTACTTCTCAGATTTCGTGTGCCAGTGC
   CCCGAAGGATTTGCTGGGAAGTGCTGTGAA
   ATAGATACTCGAGCCACGTCTGAGGGAAAC
15 AGTGACTGCTACTTTGGGAATGGGTCAGCC
   TACCGTGGTACCCACAGCCTCACCGAGTCG
   GGTGCCTCCTGCCTCCATGGAATTCCATG
   ATCCTGATAGGCAAGGTTTACACAGCACAG
   AACCCCAGTGCCCAGGCACTGGGCCTGGGC
20 AAACATAATTACTGCCGGAATCCTGATGGG
```

```
                GATGCCAAGCCCTGGTGCCACGTGCTGAAG
                AACCGCAGGCTGACGTGGGAGTACTGTGAT
                GTGCCCTCCTGCTCCACCTGCGGCCTGAGA
         5      CAGTACAGCCAGCCTCAGTTTCGCATCAAA
                GGAGGGCTCTTCGCCGACATCGCCTCCCAC
                CCCTGGCAGGCTGCCATCTTTGCCAAGCAC
                AGGAGGTCGCCCGGAGAGCGGTTCCTGTGC
                GGGGGCATACTCATCAGCTCCTGCTGGATT
        10      CTCTCTGCCGCCCACTGCTTCCAGGAGAGG
                TTTCCGCCCCACCACCTGACGGTGATCTTG
                GGCAGAACATACCGGGTGGTCCCTGGCGAG
                GAGGAGCAGAAATTTGAAGTCGAAAAATAC
                ATTGTCCATAAGGAATTCGATGATGACACT
        15      TACGACAATGACATTGCGCTGCTGCAGCTG
                AAATCGGATTCGTCCCGCTGTGCCCAGGAG
                AGCAGCGTGGTCCGCACTGTGTGCCTTCCC
                CCGGCGGACCTGCAGCTGCCGGACTGGACG
                GAGTGTGAGCTCTCCGGCTACGGCAAGCAT
        20      GAGGCCTTGTCTCCTTTCTATTCGGAGCGG
                CTGAAGGAGGCTCATGTCAGACTGTACCCA
                TCCAGCCGCTGCACATCACAACATTTACTT
                AACAGAACAGTCACCGACAACATGCTGTGT

```
        GCTGGAGACACTCGGAGCGGCGGGCCCCAG
        GCAAACTTGCACGACGCCTGCCAGGGCGAT
        TCGGGAGGCCCCCTGGTGTGTCTGAACGAT
5       GGCCGCATGACTTTGGTGGGCATCATCAGC
        TGGGGCCTGGGCTGTGGACAGAAGGATGTC
        CCGGGTGTGTACACCAAGGTTACCAACTAC
        CTAGACTGGATTCGTGACAACATGCGACCG
        TGA 3'
10      [wherein A is deoxyadenyl, G is deoxyguanyl,
        C is deoxycytidyl and T is deoxythymidyl]
```

FIG. 5F

|    |      |     |     |     |     |     |     |     |     |     |
|----|------|-----|-----|-----|-----|-----|-----|-----|-----|-----|
| H$_2$N- | | Met | Asp | Ala | Met | Lys | Arg | Gly | Leu | Cys | Cys |
|    |      | Val | Leu | Leu | Leu | Cys | Gly | Ala | Val | Phe | Val |
|    |      | Ser | Pro | Ser | Gln | Glu | Ile | His | Ala | Arg | Phe |
| 5  |      | Arg | Arg | Gly | Ala | Arg | Ser | Tyr | Gln | Val | Ile |
|    |      | Cys | Arg | Asp | Glu | Lys | Thr | Gln | Met | Ile | Tyr |
|    |      | Gln | Gln | His | Gln | Ser | Trp | Leu | Arg | Pro | Val |
|    |      | Leu | Arg | Ser | Asn | Arg | Val | Glu | Tyr | Cys | Trp |
|    |      | Cys | Asn | Ser | Gly | Arg | Ala | Gln | Cys | His | Ser |
| 10 |      | Val | Pro | Val | Lys | Ser | Cys | Ser | Glu | Pro | Arg |
|    |      | Cys | Phe | Asn | Gly | Gly | Thr | Cys | Gln | Gln | Ala |
|    |      | Leu | Tyr | Phe | Ser | Asp | Phe | Val | Cys | Gln | Cys |
|    |      | Pro | Glu | Gly | Phe | Ala | Gly | Lys | Cys | Cys | Glu |
|    |      | Ile | Asp | Thr | Arg | Ala | Thr | Ser | Glu | Gly | Asn |
| 15 |      | Ser | Asp | Cys | Tyr | Phe | Gly | Asn | Gly | Ser | Ala |
|    |      | Tyr | Arg | Gly | Thr | His | Ser | Leu | Thr | Glu | Ser |
|    |      | Gly | Ala | Ser | Cys | Leu | Pro | Trp | Asn | Ser | Met |
|    |      | Ile | Leu | Ile | Gly | Lys | Val | Tyr | Thr | Ala | Gln |
|    |      | Asn | Pro | Ser | Ala | Gln | Ala | Leu | Gly | Leu | Gly |
| 20 |      | Lys | His | Asn | Tyr | Cys | Arg | Asn | Pro | Asp | Gly |

```
        Asp Ala Lys Pro Trp Cys His Val Leu Lys
        Asn Arg Arg Leu Thr Trp Glu Tyr Cys Asp
        Val Pro Ser Cys Ser Thr Cys Gly Leu Arg
 5      Gln Tyr Ser Gln Pro Gln Phe Arg Ile Lys
        Gly Gly Leu Phe Ala Asp Ile Ala Ser His
        Pro Trp Gln Ala Ala Ile Phe Ala Lys His
        Arg Arg Ser Pro Gly Glu Arg Phe Leu Cys
        Gly Gly Ile Leu Ile Ser Ser Cys Trp Ile
10      Leu Ser Ala Ala His Cys Phe Gln Glu Arg
        Phe Pro Pro His His Leu Thr Val Ile Leu
        Gly Arg Thr Tyr Arg Val Val Pro Gly Glu
        Glu Glu Gln Lys Phe Glu Val Glu Lys Tyr
        Ile Val His Lys Glu Phe Asp Asp Asp Thr
15      Tyr Asp Asn Asp Ile Ala Leu Leu Gln Leu
        Lys Ser Asp Ser Ser Arg Cys Ala Gln Glu
        Ser Ser Val Val Arg Thr Val Cys Leu Pro
        Pro Ala Asp Leu Gln Leu Pro Asp Trp Thr
        Glu Cys Glu Leu Ser Gly Tyr Gly Lys His
20      Glu Ala Leu Ser Pro Phe Tyr Ser Glu Arg
        Leu Lys Glu Ala His Val Arg Leu Tyr Pro
        Ser Ser Arg Cys Thr Ser Gln His Leu Leu
        Asn Arg Thr Val Thr Asp Asn Met Leu Cys

```
         Ala Gly Asp Thr Arg Ser Gly Gly Pro Gln
         Ala Asn Leu His Asp Ala Cys Gln Gly Asp
         Ser Gly Gly Pro Leu Val Cys Leu Asn Asp
 5       Gly Arg Met Thr Leu Val Gly Ile Ile Ser
         Trp Gly Leu Gly Cys Gly Gln Lys Asp Val
         Pro Gly Val Tyr Thr Lys Val Thr Asn Tyr
         Leu Asp Trp Ile Arg Asp Asn Met Arg Pro -COOH
         [wherein  H₂N is amino terminal and
10       -COOH is carboxy terminal]
```

*FIG. 6C*

|    | H₂M- | Met | Asp | Ala | Met | Lys | Arg | Gly | Leu | Cys | Cys |
|----|------|-----|-----|-----|-----|-----|-----|-----|-----|-----|-----|
|    |      | Val | Leu | Leu | Leu | Cys | Gly | Ala | Val | Phe | Val |
|    |      | Ser | Pro | Ser | Gln | Glu | Ile | His | Ala | Arg | Phe |
| 5  |      | Arg | Arg | Gly | Ala | Arg | Ser | Tyr | Gln | Val | Ile |
|    |      | Cys | Arg | Asp | Glu | Lys | Thr | Gln | Met | Ile | Tyr |
|    |      | Gln | Gln | His | Gln | Ser | Trp | Leu | Arg | Pro | Val |
|    |      | Leu | Arg | Ser | Asn | Arg | Val | Glu | Tyr | Cys | Trp |
|    |      | Cys | Asn | Ser | Gly | Arg | Ala | Gln | Cys | His | Ser |
| 10 |      | Val | Pro | Val | Lys | Ser | Cys | Ser | Glu | Pro | Arg |
|    |      | Cys | Phe | Asn | Gly | Gly | Thr | Cys | Gln | Gln | Ala |
|    |      | Leu | Tyr | Phe | Ser | Asp | Phe | Val | Cys | Gln | Cys |
|    |      | Pro | Gln | Gly | Phe | Ala | Gly | Lys | Cys | Cys | Glu |
|    |      | Ile | Asp | Thr | Arg | Ala | Thr | Ser | Glu | Gly | Asn |
| 15 |      | Ser | Asp | Cys | Tyr | Phe | Gly | Asn | Gly | Ser | Ala |
|    |      | Tyr | Arg | Gly | Thr | His | Ser | Leu | Thr | Glu | Ser |
|    |      | Gly | Ala | Ser | Cys | Leu | Pro | Trp | Asn | Ser | Met |
|    |      | Ile | Leu | Ile | Gly | Lys | Val | Tyr | Thr | Ala | Gln |
|    |      | Asn | Pro | Ser | Ala | Gln | Ala | Leu | Gly | Leu | Gly |
| 20 |      | Lys | His | Asn | Tyr | Cys | Arg | Asn | Pro | Asp | Gly |

```
        Asp Ala Lys Pro Trp Cys His Val Leu Lys
        Asn Arg Arg Leu Thr Trp Glu Tyr Cys Asp
        Val Pro Ser Cys Ser Thr Cys Gly Leu Arg
 5      Gln Tyr Ser Gln Pro Gln Phe Arg Ile Ile
        Gly Gly Leu Phe Ala Asp Ile Ala Ser His
        Pro Trp Gln Ala Ala Ile Phe Ala Lys His
        Arg Arg Ser Pro Gly Glu Arg Phe Leu Cys
        Gly Gly Ile Leu Ile Ser Ser Cys Trp Ile
10      Leu Ser Ala Ala His Cys Phe Gln Glu Arg
        Phe Pro Pro His His Leu Thr Val Ile Leu
        Gly Arg Thr Tyr Arg Val Val Pro Gly Glu
        Glu Glu Gln Lys Phe Glu Val Glu Lys Tyr
        Ile Val His Lys Glu Phe Asp Asp Asp Thr
15      Tyr Asp Asn Asp Ile Ala Leu Leu Gln Leu
        Lys Ser Asp Ser Ser Arg Cys Ala Gln Glu
        Ser Ser Val Val Arg Thr Val Cys Leu Pro
        Pro Ala Asp Leu Gln Leu Pro Asp Trp Thr
        Glu Cys Glu Leu Ser Gly Tyr Gly Lys His
20      Glu Ala Leu Ser Pro Phe Tyr Ser Glu Arg
        Leu Lys Glu Ala His Val Arg Leu Tyr Pro
        Ser Ser Arg Cys Thr Ser Gln His Leu Leu
        Asn Arg Thr Val Thr Asp Asn Met Leu Cys

```
                Ala Gly Asp Thr Arg Ser Gly Gly Pro Gln
                Ala Asn Leu His Asp Ala Cys Gln Gly Asp
                Ser Gly Gly Pro Leu Val Cys Leu Asn Asp
    5           Gly Arg Met Thr Leu Val Gly Ile Ile Ser
                Trp Gly Leu Gly Cys Gly Gln Lys Asp Val
                Pro Gly Val Tyr Thr Lys Val Thr Asn Tyr
                Leu Asp Trp Ile Arg Asp Asn Met Arg Pro -COOH
                [wherein  H₂N is amino terminal and
    10          -COOH is carboxy terminal]
```

FIG. 6F

DEGRADATION OF DENATURED PROTEIN WITH IMPROVED t-PA

1 ~ 4 : PRIOR TO REACTING WITH IMPROVED t-PA
5 ~ 8 : AFTER REACTING WITH IMPROVED t-PA
1 , 5 : INACT ALBUMIN
2 , 6 : ALKALI-TREATED ALBUMIN
3 , 7 : INTACT IgG
4 ,   : ALKALI-TREATED IgG

BSA :   CALF SERUM ALBUMIN
IgG – H: IgG H-CHAIN
IgG – L: iGg L-CHAIN
⟵  :    DECOMPOSITION PRODUCT

TISSUE PLASMINOGEN ACTIVATOR AND PROCESS OF PREPARATION

This is a division of application Ser. No. 08/237,249 now U.S. Pat. No. 5,556,621, filed May 4, 1994 which is a continuation of Ser. No. 810,561 filed Dec. 20, 1991 now abandoned which is a continuation of Ser. No. 474,113 filed Apr. 27, 1990, now abandoned.

(FIELD OF THE INVENTION)

The present invention relates to a novel improved tissue plasminogen activator (improved t-PA) having a prolonged biological half life and increased stability to heat and acids which can expect an inhibitory effect against inflammation around the thrombus-formed region.

The present invention further includes deoxyribonucleic acid (DNA) coding for the said improved t-PA, a recombinant expression vector containing DNA encoding the improved t-PA, host cells transformed by said expression vector, a process for production of the improved t-PA, a drug composition comprising the improved t-PA and its use for treatment of thrombotic disease.

(BACKGROUND OF THE INVENTION)

It is known that human tissue plasminogen activator (t-PA) possesses useful fibrinolytic activity in extremely efficiently activating fibrin-bound plasminogen, while it does not efficiently activate plasminogen in the circulating body fluid phase in contrast to ordinary thrombolytic agents, streptokinase (SK) and urokinase (UK). The amino acid sequence constituting the human t-PA and nucleotide sequence of cDNA coding for human t-PA are known [Pennica, D., et al., Nature, 301, 214–221 (1983)]. It is also known that human t-PA dissolves venous and arterial blood clots. In large scale clinical tests, it is reported that human t-PA given intravenously is effective for re-perfusion of obstructive coronary artery in the patient with acute myocardial infarction.

However, a defect in applying this human t-PA to the treatment of thrombotic disease is an extremely short half life of its enzyme activity in blood. [Rijken, D. C., et al., Thromb. Heamost., 54 (1), 61 (1985), Hubert, E. F., et al., Blood, 65, 539 (1985)]. Accordingly, when used for the treatment of thrombotic disease, human t-PA should be continuously administered intravenously in a high dose.

It is known that naturally occurring human t-PA takes a domain structure, from the N-terminal of the molecule, of the finger domain, the EGF (epidermal growth factor) domain, the two domains of kringle 1 and kringle 2 and the serine protease domain, based on its fully anticipated secondary structure. It is reported by Rijken et al. [Rijken, D. C., et al., Thromb. Haemost., 54 (1), 61 (1985)] that domains of human t-PA other than the serine protease domain would be responsible for the shortness of biological half life of human t-PA. It is also reported by Zonneveld et al. [Zonneveld, A. J. V., et al., Proc. Natl., Acad. Sci. U.S.A., 83, 4670 (1986)] that the finger domain, the EGF domain and the kringle 2 domain structure would take an important role for fibrin binding activity of naturally occurring human t-PA and for maintaining fibrin-dependent activation of t-PA. However, any concrete measure for maintaining fibrin binding activity possessed by naturally occurring human t-PA and desirable properties of fibrin-dependent activity and prolonging the biological half life are unknown.

In Published Unexamined Japanese Patent Application Laid Open No. 48378/1987, there is described t-PA obtained by deletion of 87th to 175th amino acids of naturally occurring human t-PA in which kringle 1 is deleted. This t-PA is characterized by further inducing site mutation in the EGF region. The Japanese Patent Application discloses that the modified t-PA has a binding ability to fibrin and interaction with a tissue plasminogen activator inhibitor is reduced.

In EP No. 241208, there is described t-PA obtained by deletion of 92nd to 179th amino acids of naturally occurring human t-PA in which kringle 1 is deleted. It is simply mentioned that this t-PA has a fibrinolytic activity.

Furthermore, EP No. 231624 discloses modified t-PA showing a prolonged half life. The modified t-PA having F-EGF-K2-A as one of its sequence is deleted of kringle 1 but any specific process for its production is not shown. It is understood that the modified t-PA in the present invention is different from naturally occurring one in the amino acid sequence in the inter-domain region, in light of the specifically recited process.

As a result of extensive investigations, the present inventors have produced an improved t-PA which contains the finger domain, the EGF domain, the kringle 2 domain and the serine protease domain but the first kringle 1 domain is deleted at a specific amino acid site and further produced an improved t-PA which has caused site-specificmutation at the kringle 2 domain-serine protease linking site and, have succeeded in obtaining improved t-PA having excellent stability to heat and acids, having markedly prolonged biological half life and also having an antiinflammatory activity, while unexpectedly maintaining desirable properties of naturally occurring human t-PA.

(DISCLOSURE OF THE INVENTION)

The present invention relates to an improved t-PA. The improved t-PA of the present invention is quite different in its chemical structure from naturally occurring human t-PA and exhibits more excellent functions.

That is, the improved t-PA of the present invention is a polypeptide having an amino acid sequence represented by general formula below:

| $H_2N$—R— | Ser | Tyr | Gln | Val | Ile | Cys | Arg | Asp | Glu | Lys |
|---|---|---|---|---|---|---|---|---|---|---|
| | Thr | Gln | Met | Ile | Tyr | Gln | Gln | His | Gln | Ser |
| | Trp | Leu | Arg | Pro | Val | Leu | Arg | Ser | Asn | Arg |
| | Val | Glu | Tyr | Cys | Trp | Cys | Asn | Ser | Gly | Arg |
| | Ala | Gln | Cys | His | Ser | Val | Pro | Val | Lys | Ser |
| | Cys | Ser | Glu | Pro | Arg | Cys | Phe | Asn | Gly | Gly |
| | Thr | Cys | Gln | Gln | Ala | Leu | Tyr | Phe | Ser | Asp |
| | Phe | Val | Cys | Gln | Cys | Pro | Glu | Gly | Phe | Ala |
| | Gly | Lys | Cys | Cys | Glu | Ile | Asp | Thr | Arg | Ala |
| | Thr | Ser | Glu | Gly | Asn | Ser | Asp | Cys | Tyr | Phe |
| | Gly | Asn | Gly | Ser | Ala | Tyr | Arg | Gly | Thr | His |

-continued

| | | | | | | | | | |
|---|---|---|---|---|---|---|---|---|---|
| Ser | Leu | Thr | Glu | Ser | Gly | Ala | Ser | Cys | Leu |
| Pro | Trp | Asn | Ser | Met | Ile | Leu | Ile | Gly | Lys |
| Val | Tyr | Thr | Ala | Gln | Asn | Pro | Ser | Ala | Gln |
| Ala | Leu | Gly | Leu | Gly | Lys | His | Asn | Tyr | Cys |
| Arg | Asn | Pro | Asp | Gly | Asp | Ala | Lys | Pro | Trp |
| Cys | His | Val | Leu | Lys | Asn | Arg | Arg | Leu | Thr |
| Trp | Glu | Tyr | Cys | Asp | Val | Pro | Ser | Cys | Ser |
| Thr | Cys | Gly | Leu | Arg | Gln | Tyr | Ser | Gln | Pro |
| Gln | Phe | — | Y | — | Gly | Gly | Leu | Phe | Ala |
| Asp | Ile | Ala | Ser | His | Pro | Trp | Gln | Ala | Ala |
| Ile | Phe | Ala | Lys | His | Arg | Arg | Ser | Pro | Gly |
| Glu | Arg | Phe | Leu | Cys | Gly | Gly | Ile | Leu | Ile |
| Ser | Ser | Cys | Trp | Ile | Leu | Ser | Ala | Ala | His |
| Cys | Phe | Gln | Glu | Arg | Phe | Pro | Pro | His | His |
| Leu | Thr | Val | Ile | Leu | Gly | Arg | Thr | Tyr | Arg |
| Val | Val | Pro | Gly | Glu | Glu | Glu | Gln | Lys | Phe |
| Glu | Val | Glu | Lys | Tyr | Ile | Val | His | Lys | Glu |
| Phe | Asp | Asp | Asp | Thr | Tyr | Asp | Asn | Asp | Ile |
| Ala | Leu | Leu | Gln | Leu | Lys | Ser | Asp | Ser | Ser |
| Arg | Cys | Ala | Gln | Glu | Ser | Ser | Val | Val | Arg |
| Thr | Val | Cys | Leu | Pro | Pro | Ala | Asp | Leu | Gln |
| Leu | Pro | Asp | Trp | Thr | Glu | Cys | Glu | Leu | Ser |
| Gly | Tyr | Gly | Lys | His | Glu | Ala | Leu | Ser | Pro |
| Phe | Tyr | Ser | Glu | Arg | Leu | Lys | Glu | Ala | His |
| Val | Arg | Leu | Tyr | Pro | Ser | Ser | Arg | Cys | Thr |
| Ser | Gln | His | Leu | Leu | Asn | Arg | Thr | Val | Thr |
| Asp | Asn | Met | Leu | Cys | Ala | Gly | Asp | Thr | Arg |
| Ser | Gly | Gly | Pro | Gln | Ala | Asn | Leu | His | Asp |
| Ala | Cys | Gln | Gly | Asp | Ser | Gly | Gly | Pro | Leu |
| Val | Cys | Leu | Asn | Asp | Gly | Arg | Met | Thr | Leu |
| Val | Gly | Ile | Ile | Ser | Trp | Gly | Leu | Gly | Cys |
| Gly | Gln | Lys | Asp | Val | Pro | Gly | Val | Tyr | Thr |
| Lys | Val | Thr | Asn | Tyr | Leu | Asp | Trp | Ile | Arg |
| Asp | Asn | Met | Arg | Pro—COOH | | | | | |

[in the sequence, R is absent or represents:

| | | | | | | | | | |
|---|---|---|---|---|---|---|---|---|---|
| Met | Asp | Ala | Met | Lys | Arg | Gly | Leu | Cys | Cys |
| Val | Leu | Leu | Leu | Cys | Gly | Ala | Val | Phe | Val |
| Ser | Pro | Ser | Gln | Glu | Ile | His | Ala | Arg | Phe |
| Arg | Arg | Gly | Ala | Arg, | | | | | |
| Gly | Ala | Arg, | | | | | | | |
| Met, | | | | | | | | | | or,

| | | | |
|---|---|---|---|
| Met | Gly | Ala | Arg; |

Y represents A-Ile-B (wherein A represents Arg or Glu and B represents Lys or Ile);

H₂N— represents the amino terminal; and,
—COOH represents the carboxy terminal].

In the present invention, the terms "improved t-PA [II], [V], [VI] and [VIII]" are used to mean improved t-PA in which A and B are amino acids described below, respectively.

| | A | B |
|---|---|---|
| improved t-PA [II] | Arg | Lys |
| improved t-PA [V] | Arg | Ile |
| improved t-PA [VI] | Glu | Lys |
| improved t-PA [VIII] | Glu | Ile |

The improved t-PA found by the present inventors is excellent in stability to heat and acids, has markedly prolonged biological half life and also has an antiinflammatory activity, as will later be described, while maintaining desirable properties of naturally occurring human t-PA.

The present invention also aims at expressing the improved t-PA utilizing recombinant DNA manipulation. The present invention also provides novel DNA compounds coding for the improved t-PA and recombinant DNA expression vectors. The present invention also provides host cells transformed with novel cloning vectors. By the use of the DNA compounds, t-PA derivatives the presence of which are unknown so far in the natural world can be produced.

(BRIEF DESCRIPTION OF THE DRAWINGS)

FIG. 1A and FIG. 1B show base sequence of 16 oligodeoxynucleotides used for construction of synthetic gene fragment coding for Improved t-PA [II].

FIG. 2A and FIG. 2B show a synthetic gene fragment for construction of improved t-PA [II] of the invention containing restriction enzymes Bgl II and Eco RI ends at the both termini, which is constructed using 16 oligodeoxynucleotides shown in FIG. 1.

FIGS. 5A–5C and FIGS. 5D–5F show DNA base sequences encoding improved t-PA [II] and improved t-PA [V], respectively.

FIGS. 6A–6C and FIGS. 6D–6F show amino acid sequences derived from DNA base sequences encoding improved t-PA [II] and improved t-PA [V], respectively.

(BEST MODE FOR PRACTICING THE INVENTION)

Hereafter the process for production, DNA compounds and transformed cells are described below in detail. (Process for production of improved t-PA)

The gene coding for the t-PA molecule used to produce the improved t-PA molecule of the present invention was obtained from cDNA bank prepared from Bowes human melanoma cells. Poly(A)$^+$ RNA was isolated from Bowes human melanoma cells and fractionated by sucrose density gradient centrifugation. Next, a small amount of the fractionated poly(A)$^+$ RNA was taken and the mRNA fraction encoding t-PA gene was identified by the dot hybridization method using oligonucleotide probe capable of recognizing the specific sequence of t-PA mRNA. Using this t-PA mRNA-rich fraction as a starting material, cDNA bank was prepared and screened by the probe used for the identification of t-PA mRNA described above. Since no clone having the complete t-PA gene sequence was isolated, the remaining base sequence required for constructing the improved t-PA gene was synthesized with a DNA synthesizer to construct the desired gene. Then, the desired gene was constructed by the site-specific mutation induction method.

Figure 7:
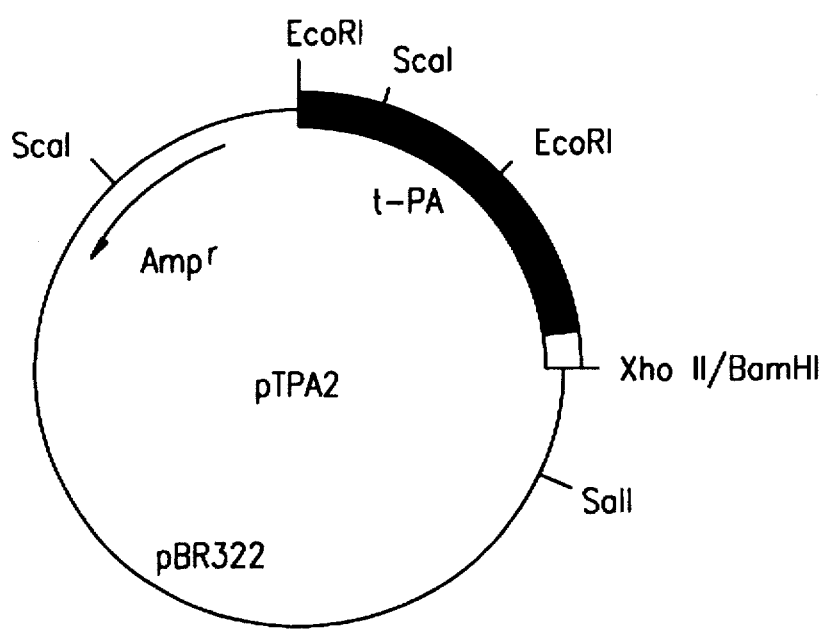
FIG. 7 shows restriction enzyme and function map of plasmid pTPA2 having integrated Eco RI-Xho II fragment (about 1,000 base pairs) of naturally occurring t-PA gene into vector pBR322 at the cleavage sites with Eco RI and Bam HI.

The Eco RI-Xho II fragment of naturally occurring t-PA gene (about 1,000 base pairs), a part of which was deleted at the N-terminal was introduced into vector pBR322 at the cleavage sites with Eco RI and Bam HI to construct pTPA2. A strain (E. coli HB 101/pTPA2) obtained by transforming E. coli with this plasmid has been deposited in the Fermentation Research Institute of the Agency of Industrial Science & Technology of Japan under Registration No. P-9649 (FERMBP-2107). Restriction enzyme and function map of plasmid pTPA2 is shown in FIG. 7.

Next, this improved t-PA gene was inserted into plasmid pVY1.

Plasmid pVY1 is obtained by ligating about 2,900 base pair Bam HI-Kpn I fragment of plasmid pKSV10 (manufactured by Pharmacia Fine Chemicals) with Eco RI cleavage fragment of plasmid pAdD26SV(A) No. 3 (N) (obtained from Dr. Hiroshi Handa of Tokyo University), after rendering both blunt ends. Accordingly, this vector contains mouse dihydrofolate reductase cDNA gene under transcription control of adenovirus (Ad2) major late promoter, SV40 early promoter upstream the improved t-PA gene inserted site and, intervening sequence or intron and polyadenylation sequence downstream.

The gene of the present invention contains genetic information for producing the improved t-PA. Therefore, the gene is integrated into an appropriate expression vector, the integrated expression vector is introduced into a suitable host cell to prepare transformants, whereby expression is effected. Thus, the improved t-PA can be produced by means of bioengineering. As host cells, prokaryotic cells such as *E. coli, Bacillus subtilis*, etc., eukaryotic microorganisms such as yeast, etc. and higher animal cells can be used. As *E. coli*, JM109 strain, W3110 Q strain, etc. belonging to K12 strain are generally used; as *Bacillus subtilis*, BD170 strain, BR151 strain, etc. are used. As yeast, RH218 strain, SHY1 strain, etc. of *Saccharomyces cerevisiae* can be utilized.

For expression with host cells, plasmid vector or phage vector containing replicon derived from species compatible with host cells and regulatory sequence are generally used. Examples of the vector for *E. coli* as the host cell include plasmids such as pBR322, pUC18, pUC19, etc.; λ phage such as λgt, Charon 4A, etc.; M13 phage, and the like. As the vector for *Bacillus subtilis*, pUB110, pSA2100, etc. can be used and as the vector for yeast, YRp7, YEp61, etc. can be used.

The vector must bear a promoter capable of expressing the desired protein. As the promoter for *E. coli* gene or phage gene, for example, lac, trp, tac, trc, PL, etc. can be utilized.

In the case of using culture cells of higher animal as the host, kidney cells of rhesus monkey, mosquito larva cells, kidney cells of African green monkey, mouse fetal fibroblast, Chinese hamster ovary cells, human fetal kidney cells, moth oval tissue cells, human cervical epithelium-like cells, human myeloma cells, mouse fibroblasts, etc. are used. As the vector, there can be used SV40 early promoter, SV40 late promoter, SV40 bearing a promoter from eukaryotic gene (for example, estrogen-inducing avian ovalbumin gene, interferon gene, glucocorticoid-inducing tyrosine aminotransferase gene, thymidine kinase gene, adenovirus early and late genes, phosphoglycerate kinase gene, a factor gene, etc.), bovine papilloma virus or derivative vectors thereof and the like.

It is further known that t-PAs secreted and produced by cells have various N-termini, depending upon difference in cleavage sites.

As the N-terminal sequences that are generally known, there are the amino acid sequence of the present invention in which R is absent or in which R is absent and 3 amino acids (Ser Tyr Gln) at the N-terminal end are further cleaved and the N-terminal begins with Val or in which R is Gly Ala Arg; and the like.

As such, in the case of secreting and producing t-PA using culture cells as the host, the way of cleavage with signal peptidase or protease varies depending upon kind of cells so that t-PA species having different N-termini may also be produced.

This phenomenon is not applied only to the case of secretion and production by culture cells but it is considered that a similar phenomenon would also occur with respect to the way of the N-terminal of t-PA produced by *E. coli*, *Bacillus subtilis*, yeast, and other cells being modified.

For transformation of the host using the expression vector having integrated therein the improved t-PA gene, the Hanahan method [Hanahan, D., J. Mol. Biol., 166, 557 (1983)] can be adopted in the case of *E. coli*; in the case of animal cells, the calcium phosphate method [Van der Eb, A. J. and Graham, F. L., Method in Enzymology, 65, 826 (1980), academic Press], etc. can be adopted.

The DNA sequence and plasmid explained in the present invention can be subjected to various modifications and variations. For example, it is possible to substitute the nucleotide over the entire regions encoding polypeptide because of synonymity of the gene; at the same time, it is also possible to replace

translation termination signal for

translation termination signal specifically exemplified. Such a sequence can be presumed from the amino acid or DNA sequence of human t-PA currently known and can be constructed by conventional DNA synthesis method. Accordingly, the base sequence of the gene of the present invention is not limited to only one DNA sequence in any sense.

As described above, the improved t-PA is useful for the treatment of various acquired diseases involving vascular coagulation including deep vein, pulmonary arterial embolism, peripheral arterial thrombosis, heart or peripheral artery-derived embolism, acute myocardial infarction and thrombotic attack.

Like naturally occurring human t-PA, the improved t-PA is particularly useful for treatment of acute myocardial infarction. As has recently been proven, naturally occurring human t-PA is effective for dissolution of occlusive coronary arterial thrombus, regeneration of myocardiac perfusion and recovery of most parts in ischemic myocardiac layer, when intravenously administered in a dose of 30 to 70 mg over 1 to 3 hours. The improved t-PA has a markedly prolonged half life in blood and is thus effective as in naturally occurring human t-PA. It is expected that the improved t-PA would, be as effective clinically as with naturally occurring human t-PA, in a dose of about 10% of the dose recommended with naturally occurring human t-PA even in a single administration.

In addition, the improved t-PA of the present invention further exhibits the following useful properties that are unknown so far with naturally occurring human t-PA and modified t-PAs.

a) Antiinflammatory activity

In the thrombus region, not only formation of the thrombus but also formation of fibrin degradation products or a trace amount of kinin, etc. are recognized. It is known that these substances have an inflammation-inducing activity and thus cause inflammation in the thrombus region. For such a reason, it is desired that a thrombolytic agent used for treatment of thrombosis should possess not only a thrombolytic activity but also an antiinflammatory activity.

As a result of extensive investigations, the present inventors have succeeded in imparting the antiinflammatory activity based on the two functions to the improved t-PA.

One is the experimental fact that the improved t-PA inhibits the biological activity of interleukin 1 (IL-1) which is one of mediators for inflammatory reaction. IL-1 produced in macrophage is considered to participate in inflammatory reaction via pyrexia, acceleration of growth of fibroblast, production of colagenase in synovial cell membrane, etc., or acceleration of synthesis of prostacycline in vascular endothelial cells. It is also known that IL-1 acts on liver cells to accelerate the production of proteins (serum amyloid protein, fibrinogen, etc.) in the acute phase which increased upon inflammation. Now the present inventors have found that the improved t-PA inhibits the activity (LAF activity) of enhancing mitogen reactivity of mouse thymocyte, which is one of the biological activities of IL-1.

Another is that the improved t-PA has affinity to denatured protein (denatured IgG, denatured albumin, etc.) caused by inflammation in the thrombus region and additionally possesses the property of being activated by the denatured protein.

By this activity, the improved t-PA does not act on protein that undergoes no denaturation but decomposes only denatured protein in the inflammatory region, and inflammation can be palliated. The present inventors have confirmed by SDS gel electrophoretic analysis that the improved t-PA decomposes the denatured protein alone.

Figure 13:
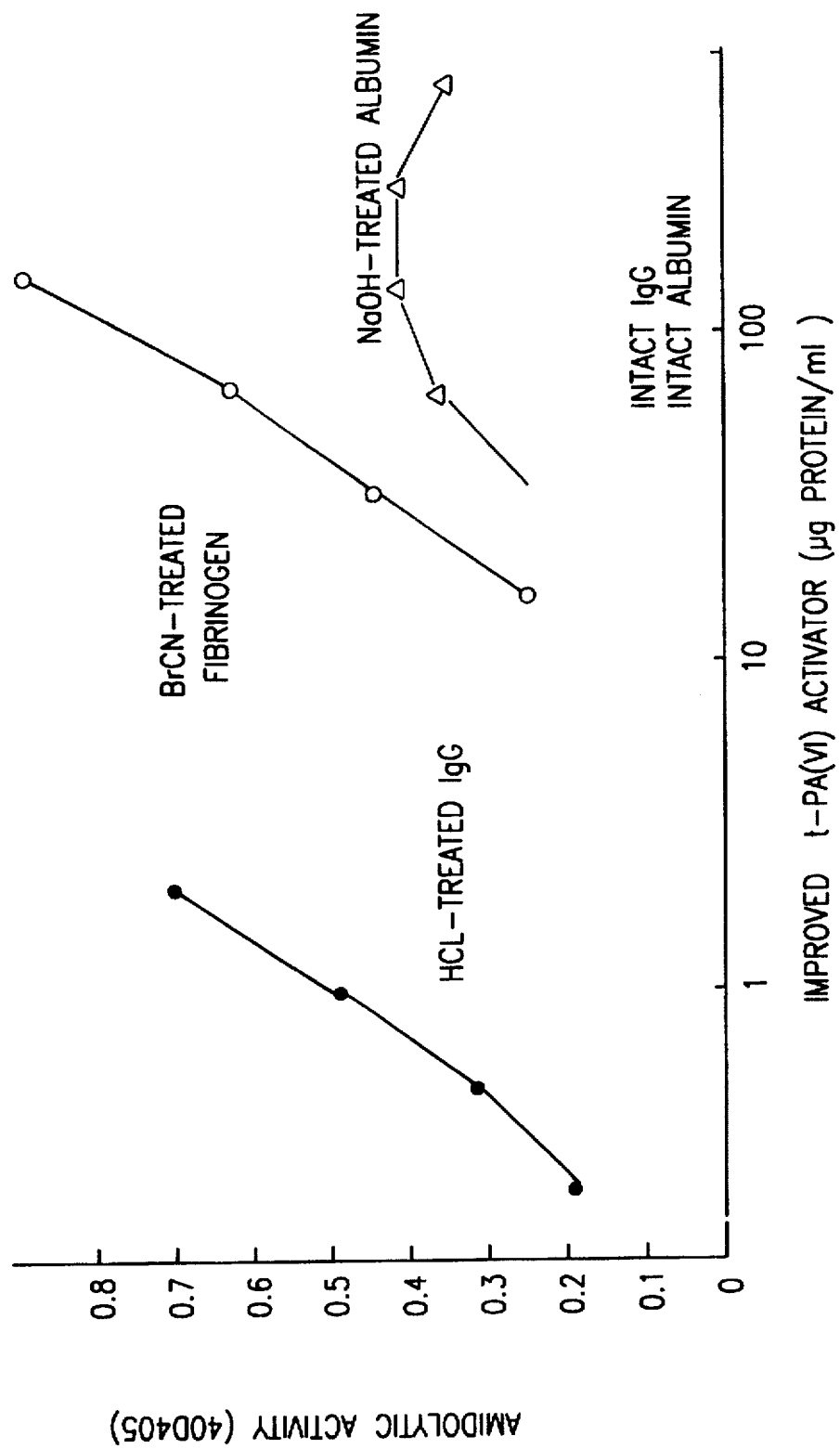
FIG. 13 shows activated state of improved t-PA [VI] with denatured protein.

As shown in FIG. 13, the activation activity and selectivity of the improved t-PA by denatured protein are remarkable. In HCl-treated IgG, similar activity was shown in a concentration reduced by one-several tenth of BrCN-treated fibrinogen. On the other hand, normal IgG did not develop the activation action to the improved t-PA even in a concentration of 500 μg/ml.

b) Prevention of reocclusion after the reperfusion of occluded blood vessel

It is known that when thrombosis was treated by natural t-PA, reocclusion was noted with high frequency after reperfusion of the occluded blood vessel. For this reason, combined therapy with a platelet coagulation inhibitor or an anticoagulant has been performed under the actual situation. However, the combined therapy involves problems of interaction of drugs, dose control, side effects, etc. Rather, it is more desired that t-PA itself additionally possesses the activity of preventing from causing reocclusion.

The improved t-PA of the present invention has per se the activity of preventing from causing reocclusion, based on the mechanism on two types of activities.

Part 1) The first is to prevent rapid reduction in t-PA concentration after administration of the improved t-PA by the prolonged durability, thereby to get rid of rebound phenomenon and thus prevent from occurrence of reocclusion.

Part 2) The second is that by preventing impairment of vascular endothelial cells caused by IL-1, platelet coagulation is indirectly inhibited thereby to prevent occurrence of reocclusion.

c) Enhanced stability

Protein preparations are generally unstable so that it is required to preserve the preparations in a freeze dried state or at low temperatures in a solution state. It is expected that a plasminogen activator is administered to the patient with acute myocardiac infarction and in this case, it is considered to be necessary that the plasminogen activator should be administered within several hours after the onset of attack, in order to reduce the mortality rate. Therefore, the plasminogen activator preparations should be stored in various places but depending upon place, it may occur that facilities for storing at low temperature might not be utilizable. In such a case, stable preparations that can be stored at room temperature are desired.

Further when the stability is improved, it is possible to perform heat treatment, treatment with acids, etc. during the course of making preparations. Particularly in the improved t-PA of the present invention which is produced by cell culture, it becomes possible to remove cell-derived retrovirus known to be weak against heat.

Hereafter the present invention is described more specifically with reference to the examples below but is not deemed to be limited thereto. Unless otherwise indicated, recombinant DNA is produced by the laboratory manual described below.

Maniatis, T., et al., Molecular Cloning: A Laboratory Manual, Cold Spring Harbor Laboratory, Cold Spring Harbor, N.Y. (1982)

EXAMPLE 1

Cloning of t-PA cDNA

Bowes human melanoma cells (acquired from Dr. Roblin, R. in the National Cancer Institute, USA) are cultured in a manner similar to the method of Opdenakker et al. [Opdenakker, G., et al., Eur. Biochem., 131, 481–487 (1983) ]. In order to induce t-PA mRNA, TPA (12-O-tetradecanoylphorbol 13-acetate) is added to the culture in the final concentration of 100 ng/ml followed by culturing for 16 hours. Next, the total cell RNA is extracted from the culture cells according to the modified method of Freeman et al. [Okayama/Berg cDNA Manual, page 3 (1985), Pharmacia Fine Chemicals]. Using oligo-dT cellulose column (manufactured by Pharmacia Fine Chemicals), poly(A)$^+$ RNA is separated from the total cell RNA. As the result, about 400 µg of poly(A)$^+$ RNA is obtained from approximately $10^9$ cells.

This poly(A)$^+$ RNA is fractionated by sucrose density gradient centrifugation in a conventional manner. A part of the fractionated poly(A)$^+$ RNA is taken and the dot blot hybridization [Perbal, B., A Practical Guide to Molecular Cloning, 410 (1984), John Wiley & Sons, Inc.] is performed using oligonucleotide probe specific to t-PA mRNA to estimate the t-PA mRNA fraction. The probe (probe Y) used in this case has a base sequence of 5'-GCTTGGCAAAGATGGCA-3' which is complementary to the mRNA region encoding the +291 to +297 amino acid sequence of t-PA reported by Pennica et al. supra and synthesized by the β-cyanophosphamidide method using Model 380A DNA Synthesizer (manufactured by Applied Biosystems). Synthesis of DNA oligomer, removal of protection group, cleavage from resin and purification are carried out as instructed by the manual for Model 380A DNA Synthesizer. Radioactive label of probe Y at the 5'-terminal is performed according to the Laboratory Manual, page 122, using T4 polynucleotide kinase (manufactured by Takara Shuzo Co., Ltd.) and γ-[$^{32}$P] ATP.

Probe Y is strongly hybridized mainly with 20 to 30S poly(A)$^+$ RNA (this fraction is called Fraction M).

Using as a template 10 µg of poly(A)$^+$ RNA obtained from Fraction M, 3 µg of double stranded cDNA is synthesized using reverse transcriptase (manufactured by Biochemical Industry Co., Ltd.) according to the Gubler-Hoffman method [Gubler, U. and Hoffman, B. J., Gene, 25, 263 (1983)] and, deoxy C chain is added to the double stranded cDNA at the 3'-terminal thereof according to the method of Deng-Wu [Deng, G. R. and Wu, R., Nucleic Acids Res., 9, 4173 (1981)]. Next, the deoxy C chain-added double stranded cDNA is subjected to gel filtration on CL4B Sepharose (manufactured by Pharmacia Fine Chemicals) to remove low molecular nucleic acids having base pairs less than about 500. Thereafter, the cDNA is subjected to annealing with pBR322 (manufactured by Bethesda Research) added with deoxy G chain at the Pst I site in a conventional manner. Using the mixture resulting after the annealing, E. coli HB101 competent cells (manufactured by Takara Shuzo Co., Ltd.) are transformed. As the result, cDNA bank composed of about 40,000 independent transformants is obtained.

This cDNA is subjected to colony hybridization using probe Y described above according to the method of Woods [Woods, D., Focus, 6(3), 1 (1984); manufactured by Bethesda Research Lab.] to obtain clones reacted with probe Y. Among the clones, a base sequence of the cDNA region is determined with respect to plasmid pTPA1 of clone containing the longest t-PA cDNA. The method followed the dideoxy method [Carlson, J., et al., J. Biotechnology, 1, 253 (1984)] using M13 phage vector and the 7-DEAZA method [Mizusawa, S., et al., Nucleic Acids Res., 14, 1319 (1986)]. As the result, it is noted that plasmid pTPA1 contained the base sequence from T at +441 to A at +2544 for t-PA gene reported by Pennica et al. supra.

EXAMPLE 2

Construction of Improved t-PA [II]

In plasmid pTPA1 shown in Example 1, the N-terminal region is insufficient to construct t-PA (improved) [II] which is deleted of the kringle 1 domain. Therefore, the insufficient DNA segment is synthesized as described above using 380A DNA Synthesizer (manufactured by Applied Biosystems). The base sequence of the synthesized oligomer and the entire synthesized sequence are shown in FIGS. 1 and 2, respectively. Furthermore, specific procedures for construction of the improved t-PA [II] using these oligomers are shown in FIGS. 3-1 and 3-2, respectively.

2-1) Construction of Block IV (Bgl II-Eco RI Fragment, about 480 Base Pairs)

Figure 3A:
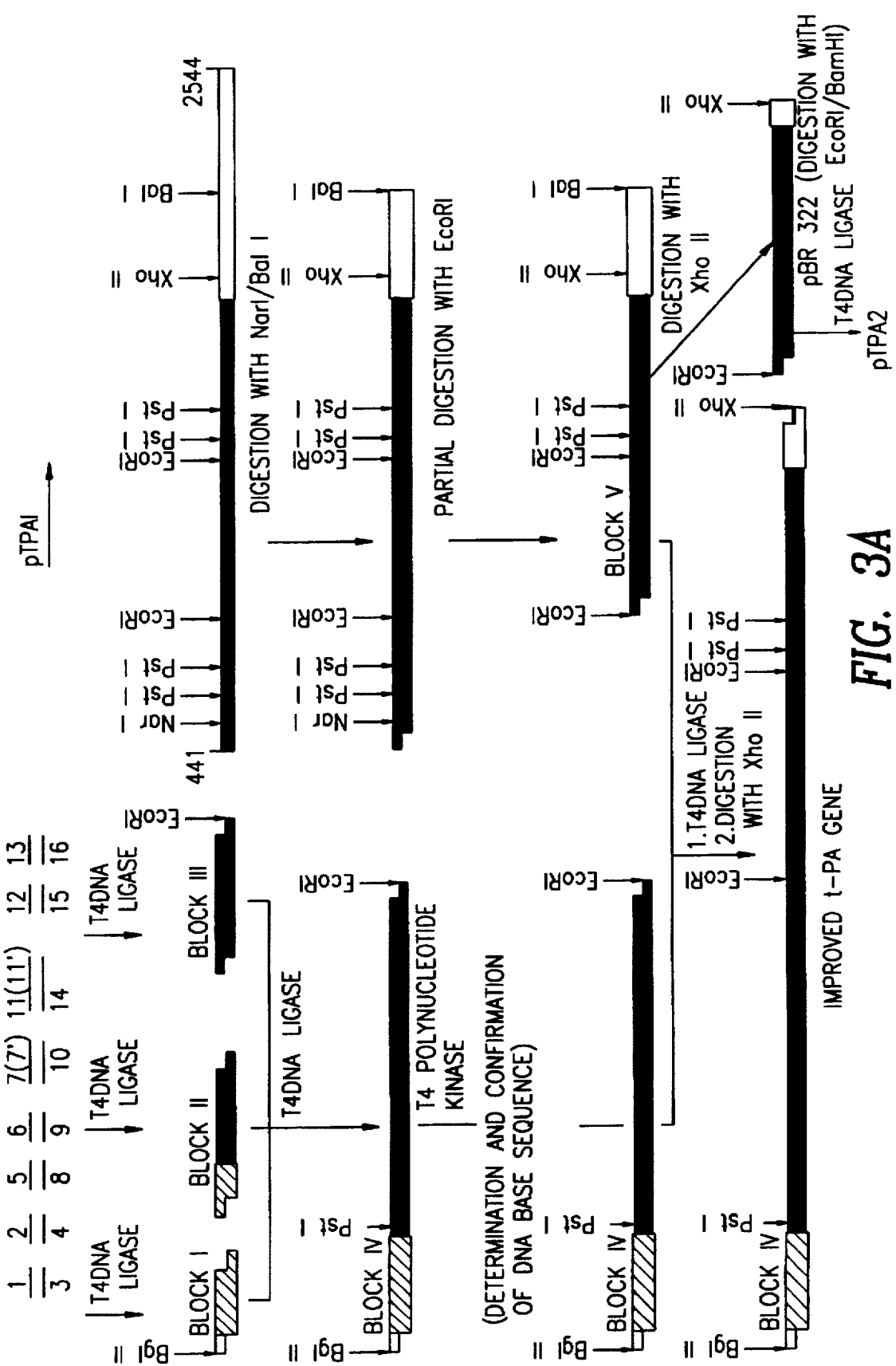
FIG. 3A shows the procedure for constructing improved t-PA [II]. In the figure, black portions oblique portion and white-on-black portion denote a region encoding mature t-PA protein, a region encoding prepropeptide and a nontranslation region, respectively.
Figure 3B:
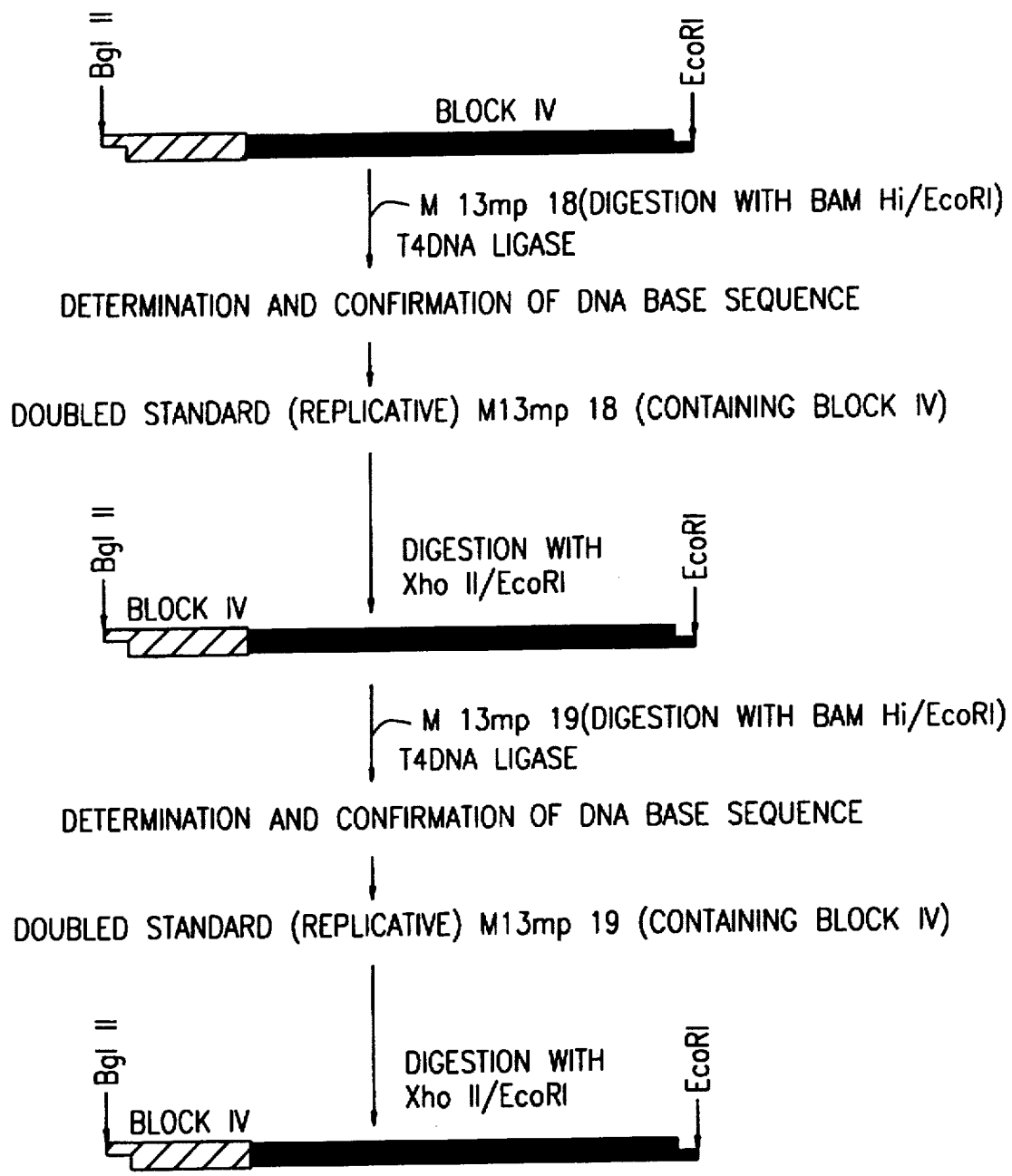
FIG. 3B shows a method for verification of synthetic gene fragment block IV through determination of DNA base sequence by the dideoxy method and the 7-DEAZA method.

Block IV fragment in FIG. 3-1 is prepared as follows.

Firstly, according to the Laboratory Manual, page 122, 40 pmoles each of synthetic oligonucleotides 2, 3, 4, 5, 6, 7, (7'), 8, 9, 10, 11, (11'), 12, 13, 14 and 15 shown in FIG. 1 is phosphorylated with 10 units of T4 polynucleotide kinase (manufactured by Takara Shuzo Co., Ltd.) at 37° C. for an hour in 50 ml each of reaction solution. The reaction solution is treated with phenol. After ethanol precipitation, the precipitates are dried under reduced pressure and dissolved in sterile distilled water. After allowing to stand 40 pmoles each of the oligomer in 150 µl of a solution containing 7 mM Tris-HCl (pH 7.5), 20 mM NaCl, 7 mM MgCl$_2$ and 0.1 mM EDTA at 80° C. for 5 minutes, at 60° C. for 5 minutes and at room temperature for an hour in the respective blocks of block I (oligomers 1, 2, 3 and 4), block II (oligomers 5, 6, 7 (7'), 8, 9 and 10) and block III (oligomers 11, (11'), 12, 13, 14, 15 and 16), ethanol precipitation and drying under reduced pressure follow. The residue is dissolved in 40 µl of sterile distilled water. The reaction is carried out in 400 µl of the reaction solution at 4° C. for 15 hours using DNA ligation kit (manufactured by Takara Shuzo Co., Ltd.). After ethanol precipitation and drying under reduced pressure, the residue is dissolved in sterile distilled water: in the case of block I (1), gel electrophoresis is carried out in a concentration of 5% polyacrylamide (Laboratory Manual supra, page 173) and the fragment of about 100 base pairs is separated and isolated in a conventional manner (Laboratory Manual supra, page 178); and in the case of block II (2) and block III (3), gel electrophoresis is carried out in a concentration of 3% agarose gel (LMP Agarose, manufactured by BRL) (Laboratory Manual supra, page 150) and the fragments of about 190 base pairs are separated and isolated by electric elution, respectively. (Laboratory Manual supra, page 164).

Next, 0.1 μg, 0.2 μg and 0.2 μg of the fragments of block I, block II and block III isolated, respectively, are ligated using the aforesaid DNA ligation kit. Then, gel electrophoresis is carried out in a concentration of 1.5% agarose to separate Bgl II-Eco RI fragment (block IV) of about: 480 base pairs. Then, DNA is isolated from the agarose gel by electric elution. This DNA is further phosphorylated in 100 μl of the reaction solution at 37° C. for an hour using 10 units of the aforesaid T4 polynucleotide kinase followed by phenol treatment, ethanol precipitation and drying under reduced pressure.

This synthetic gene segment and the base sequence of block IV are confirmed by determining the base sequence according to the dideoxy method using M13 phage vector and the 7-DEAZA method. Specific procedures are shown in FIG. 3-2. After the block IV Bgl II-Eco RI fragment described above is ligated with M13mp18 DNA (manufactured by Boehringer Mannheim-Yamanouchi Co., Ltd.) cleaved with restriction enzymes Bam HI (manufactured by Boehringer Mannheim-Yamanouchi Co., Ltd.) and Eco RI (manufactured by Boehringer Mannheim-Yamanouchi Co., Ltd.) using the DNA ligation kit described above, its base sequence is determined using M13 sequence kit (manufactured by Takara Shuzo Co., Ltd.) and 7-DEAZA sequence kit (manufactured by Takara Shuzo Co., Ltd.).

The restriction enzyme Bgl II cleavage site and the Bam HI cleavage site are ligated by isoshizomer arrangement via [Bam HI cleavage end

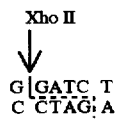

Bgl II cleavage site] and the ligated fragment can be cleaved with restriction enzyme Xho II, whereby the original Bgl II cleavage end and the Bam HI cleavage end appear, respectively.

In order to determine the base sequence more precisely, M13mp18 (including block IV fragment) phage is further infected to E. coli JM109 according to the method of Messing [Messing, J., Methods in Enzymology, 101, 20–78 (1983)] and double stranded DNA (replication type) is then produced. After this DNA (50 μg out of the produced DNA) is cleaved with restriction enzymes Xho II (manufactured by Boehringer Mannheim-Yamanouchi Co., Ltd.) and Eco RI, gel electrophoresis is performed in 1.5% agarose concentration to separate about 480 base pairs of fragment (block IV). This DNA is recovered by electric elution. After ligating the recovered DNA with M13mp19-DNA (manufactured by Boehringer Mannheim-Yamanouchi Co., Ltd.) cleaved with restriction enzymes Eco RI and Bam HI in a manner similar to above using the DNA ligation kit, its base sequence is determined. As described above, it can be verified to have an accurate base sequence by determining both DNA sequences using M13mp18 and M13mp19. Furthermore, M13mp19 (including block IV) double stranded replicative DNA is produced by the method described above. After cleaving this DNA (50 μg out of the product produced) with restriction enzymes Eco RI and Xho II, 1.5% agarose gel electrophoresis is carried out to separate about 480 base pairs of fragment (block IV). DNA is isolated by electric elution.

2-2) Isolation of Block V (Eco RI-Bal I Fragment, about 1250 Base Pairs)

From clone pTPA1 obtained in Example 1, plasmid DNAs are produced in large quantities according to the method described in the Laboratory Manual supra at page 86, as shown in FIG. 3-1. After cleaving 70 μg of this DNAs with restriction enzymes Bal I (manufactured by Takara Shuzo Co., Ltd.) and Nar I (manufactured by Nippon Gene Co., Ltd.), 0.8% agarose gel electrophoresis is carried out to separate the Nar I-Bal I fragment (about 1540 base pairs). DNA is isolated by electric elution. After further partially digesting this DNA with restriction enzyme Eco RI, 0.8% agarose gel electrophoresis is carried out to separate the Eco RI-Bal I fragment: (about 1250 base pairs). DNA is isolated by electric elution.

2-3) Construction of improved t-PA [II] gene from block V and block IV

As shown in FIG. 3-1, the improved t-PA gene is produced as follows.

After ligating block IV (Bgl II-Eco RI fragment, about 480 base pairs) obtained in Example 2-1) with block V (Eco RI-Bal I fragment, about 1250 base pairs) obtained in Example 2-2) using the DNA ligation kit described above, the ligated product is subjected to ethanol precipitation. After drying under reduced pressure, the precipitate is cleaved with restriction enzyme Xho II in a conventional manner. Next, 0.8% agarose gel electrophoresis is carried out to separate the Bgl II-Xho II fragment (about 1,500 base pairs, containing improved t-PA gene). DNA is then isolated by electric elution. The entire base sequence of the thus constructed improved t-PA [II] gene is shown in FIG. 5. A deduced amino acid sequence is also shown in FIG. 6.

EXAMPLE 3

Construction of Improved t-PAs [V], [VI] and [VIII] Gene

Constructions of the improved t-PAs [V], [VI] and [VIII] gene are carried out based on the improved t-PA [II] gene, by referring to the following publications.

The desired genetic conversion is performed by the site-specific mutation induction method.

Publications:

Zoller, M. J. and Smith, M., Method in Enzymology, 100, 468–500 (1983); Zoller, M. J. and Smith, M., DNA, 3, 479–488 (1984); Morinaga, Y., et al., Bio/technology, 636–639 (July 1984); Adelman, J. P., et al., DNA, 2, 183–193 (1983); M13/pUC Sequence Manual [issued by Nippon Gene Science Room Co., Ltd.]

3-1) Construction of Improved t-PA [V] Gene

A) Design of M13mp9 (improved t-PA [II]) capable of inducing mutation

Figure 8:
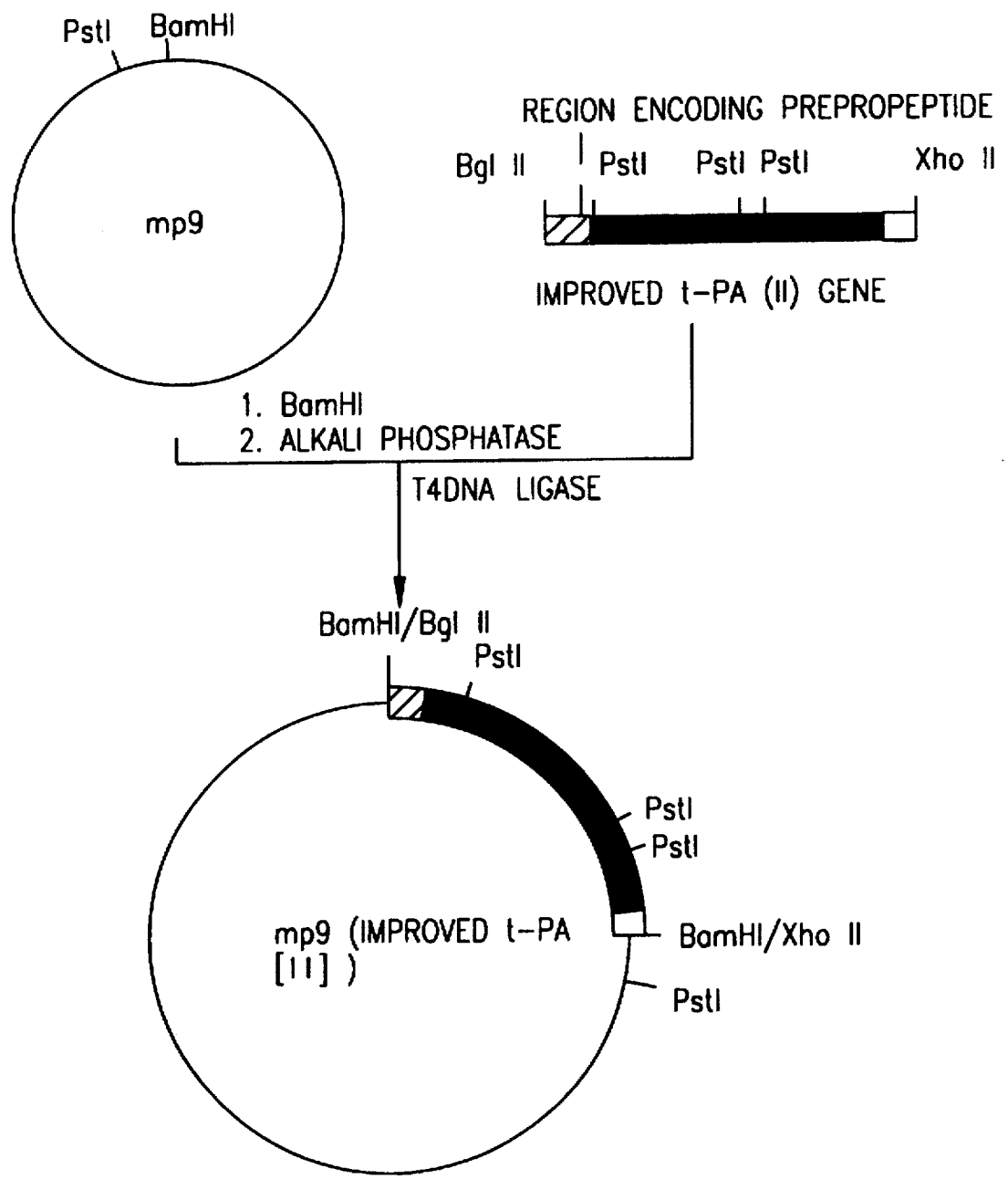
FIG. 8 shows mp9 (improved t-PA [II]) having integrated Bgl II-Xho II fragment (about 1,500 base pairs) of improved t-PA [II] gene into double stranded M13mp9 DNA at the cleavage site with Bam HI.

The improved t-PA [II] gene fragment described in detail in Example 2, 2-3) is ligated with double stranded M13mp9 DNA treated with restriction enzyme Bam HI and with alkaline phosphatase (manufactured by Takara Shuzo Co., Ltd.) using the DNA ligation kit described above. The ligation product described above is transfected in *E. coli* JM109 competent cells (manufactured by Takara Shuzo Co., Ltd.). Each clone of the resulting colorless phage plaque is infected to *E. coli* JM109. Single stranded DNA is isolated from the culture supernatant and double stranded (replicative) DNA is isolated from the *E. coli* cells according to the method of Messing [Messing, J., Methods in Enzymology, 101, 20–78 (1983)]. By pattern analysis of these double stranded DNAs after cleavage with restriction enzyme (Pst I) by agarose gel electrophoresis, clone, mp9 (improved t-PA [II]), in which improved t-PA [II] is inserted into mp9 DNA in the desired direction as shown in FIG. 8, is obtained.

That is, after cleaving a part of these DNAs with restriction enzyme Pst I, 0.8% agarose gel electrophoresis is; carried out to give clone mp9 (improved t-PA [II]) showing a single band, respectively, at about 7,300 base pairs, about 840 base pairs, about 430 base pairs and about 80 base pairs Single stranded DNA of this clone is used in the subsequent experiment for inducing the site-specific mutation.

B) Synthesis of primer capable of inducing site-specific mutation

Synthetic oligonucleotide used for causing site-specific mutation of the improved t-PA [II] gene is synthesized by the β-cyanoethylphosphoamidide method using Model 380A DNA Synthesizer (manufactured by Applied Biosystems). Synthesis of DNA oligomer, removal of protection group, cleavage from resin and purification are carried out as instructed by the manual for Model 380A DNA Synthesizer. To induce mutation at the specific site, primer ① capable of inducing the following site-specific mutation and primer ② for sequencing by the dideoxy method using M13 phage vector [Carlson, J., et al., J. Biotechnology, 1, 253 (1984)] are prepared.

5'-Terminal phosphorylation of synthetic oligomer

The DNA of primer ① for inducing site-specific mutation is phosphorylated by the procedure described in Example 2, 2-1).

Production of heteroduplex DNA

Single stranded M13mp9 (improved t-PA [II]) DNA, 0.5 µg, and 1.5 µg of double stranded M13mp9 DNA cleaved with restriction enzyme Bar HI are heated in 30 µl of solution containing 2 pmoles of the phosphorylated primer ① for inducing mutation, 10 mM Tris-HCl (pH 7.5), 0.1 mM EDTA and 50 mM NaCl at 90° C. (2 minutes), at 50° C. (5 minutes), at 37° C. (5 minutes) and at room temperature (10 minutes). To the solution is added 36 µl of a solution of 50 mM Tris-HCl (pH 8.0) containing 4 units of Klenow enzyme, 7 units of T4 DNA ligase, 0.1 mM EDTA, 12 mM MgCl$_2$, 10M dithiothreitol, 0.7 mM ATP, 0.07 mM dATP and 0.2 mM each of dGTP, dTTP and dCTP to initiate primer elongation. The mixture is reacted at 20° C. for 2 hours and at 4° C. for 15 hours.

Transformation was performed using the solution described above and *E. coli* JM109 competent cells (manufactured by Takara Shuzo Co., Ltd.) to form plaque. After picking up colorless plaque, phage is infected to *E. coli* JM109 to proliferate the same. Thereafter, template single stranded DNA is produced from the culture supernatant with respect to each clone. These single stranded DNAs are subjected only to Reaction "T" [Reactions "A" and "T" in Example 3-2] of the Dideoxy method using primer ② for sequencing followed by polyacrylamide gel electrophoresis. After drying, the gel is analyzed by autoradiography. Based on the results, clone having the objective mutation sequence is identified. With respect to this clone, the culture supernatant described above is infected to *E. coli* JM109 and

| | | | | | | | | |
|---|---|---|---|---|---|---|---|---|
| Amino acid sequence of improved t-PA [II]: | Gln Phe | Phe | Arg | Ile | Lys | Gly | Gly | Leu |
| DNA sequence of improved t-PA [II]: | T CTC | CAG TTC | TTT GC | CGC | ATC | AAA | GGA | GGG |
| | | | | | | Ile | | |
| DNA sequence of primer ①5' for inducing mutation: | T CTC | CAG TTC | TTT GC | CGC 3' | ATC | A$\underline{T}$A | GGA | GGG |
| DNA sequence of primer ②5' for sequencing: | GCA | GGC | TGA | CGT | GGG | AG | 3' | |

The amino acid sequence of improved t-PA [II] and gene sequence are described in the foregoing two rows. The primer ① capable of inducing mutation is different in the underlined base from the gene sequence for improved t-PA [II].

c) Induction of site-specific mutation

Hereafter shown is a way to construct a clone containing the base sequence of primer ① capable of inducing mutation, namely, improved t-PA [V] gene. After annealing mp9 (improved t-PA [II]) single stranded DNA described in Example 3, 3-1), A) and the primer ① capable of inducing mutation, the annealed product is converted into double stranded DNA, which is then transformed in *E. coli* JM109. Next, using the primer for sequencing, screening is carried out by DNA sequencing to isolate phage clone bearing the mutated improved t-PA [II] gene, namely, improved t-PA [V] gene. From this clone, double stranded (replicative) phage DNA is produced and this improved t-PA [V] gene is isolated.

inoculated onto a plate to again perform isolation of a single plaque. Regarding the resulting clone of single plaque, single stranded DNA is produced as described above. Using these DNAs, DNA base sequence is firstly determined by the dideoxy method using primer ② for sequencing to obtain a clone mutated into the desired base sequence. After this phage clone is infected to *E. coli* JM109 using the method of Messing as described in Example 2, double stranded DNA is produced. This double stranded DNA is cleaved with restriction enzyme Xho II, 0.8% agarose gel electrophoresis is carried out to isolate a fragment (improved t-PA [V] gene) about 1500 base pairs containing improved t-PA gene. Thereafter, DNA is recovered by electric elution.

Furthermore, the entire base sequence is determined by the dideoxy method, with respect to the thus produced DNA, whereby it is confirmed that the DNA is improved t-PA [V] gene. The entire base sequence of the thus constructed improved t-PA [V] gene (but containing signal peptide −35 to −1) is shown in FIG. 5-2. The amino acid sequence deduced therefrom is also shown in FIG. 6-2.

3-2) Construction of Improved t-PAs [VI] and [VIII]

| | | | | | | | | |
|---|---|---|---|---|---|---|---|---|
| Amino acid sequence of improved t-PA [II]: | | Gln Gly | Pro | Gln | Phe | Arg | Ile | Lys Gly |
| DNA sequence of improved t-PA [II]: | GC | CAG GGA | CCT GGG | CAG C | TTT | CGC | ATC | AAA |
| DNA sequence of primer ③ 5' for inducing mutation: | GC | CAG GGA | CCT GGG | CAG C | TTT 3' | Glu GAA | ATC | AAA |
| DNA sequence of primer ⑤ 5' for sequencing: | GC | CAG GGA | CCT GGG | CAG C | TTT 3' | Glu GAA | ATC | Ile ATA |

The procedures are similar to those described in Example 3, 3-1). Firstly, M13mp9 (improved t-PA [II]) is constructed for inducing mutation and primers for inducing site-specific mutation are then synthesized. The base sequence of these primers are described above but for construction of improved t-PA [VI] gene and improved t-PA [VIII] gene, 5'-end phosphorylated primer ③ for inducing mutation and 5'-end phosphorylated primer ⑤ for constructing improved t-PA [VIII] gene are used, respectively. Further after site-specific mutation induction, the entire base sequence is determined by the Dideoxy method and it is confirmed that they have the desired base sequences. The improved t-PAs [VI] and [VIII] are thus produced.

Next, these genes are integrated into vector pVY1 according to the procedures described in Examples 4 and 5 in detail.

EXAMPLE 4

Integration of Improved t-PA [II] Gene into Vector pVY1

4-1) Construction of Vector pVY1

Figure 4:
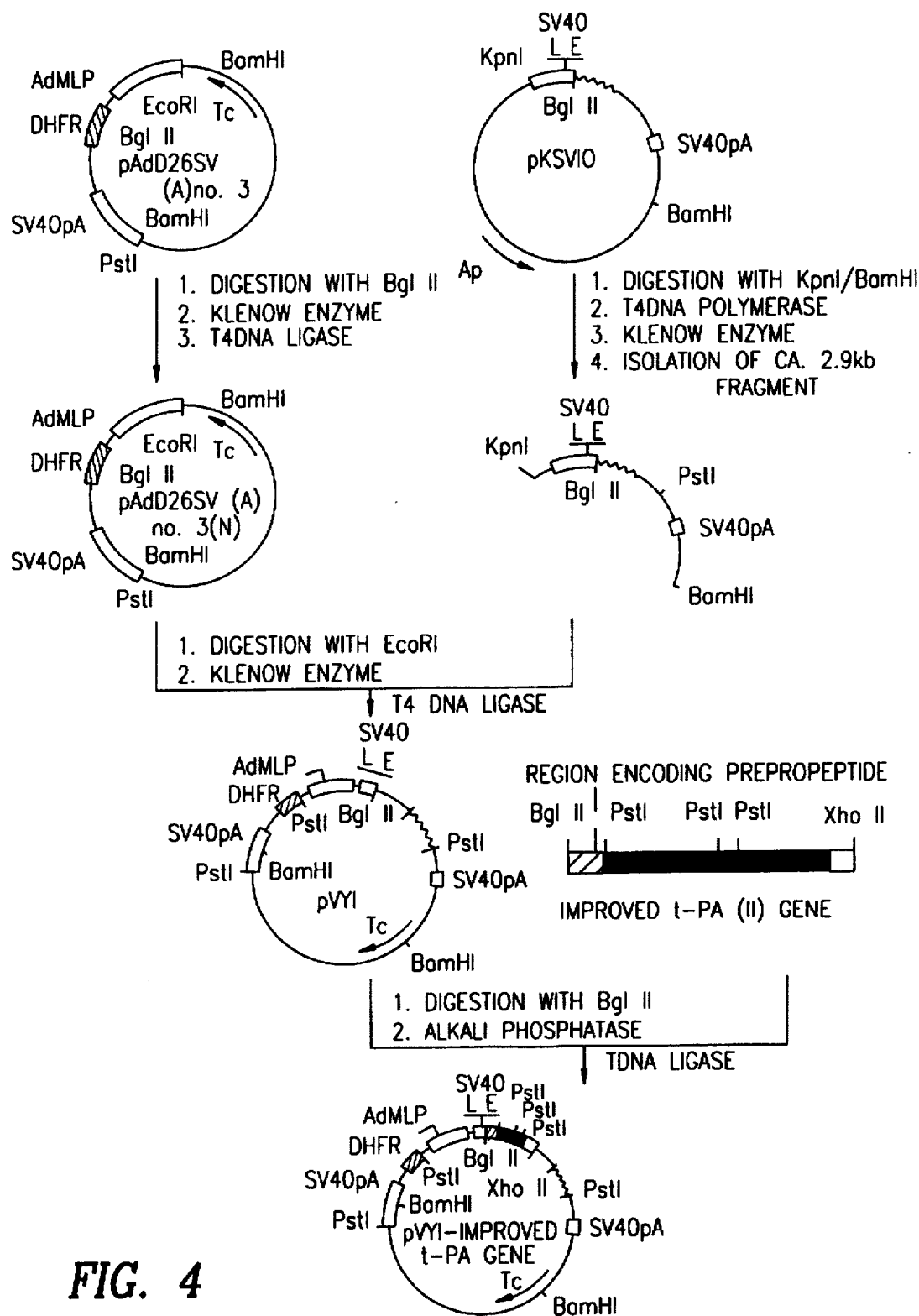
FIG. 4 shows the procedure for constructing expression vector pVY1 in animal cells and integration of improved t-PA into pVY1.

Vector pVY1 is prepared as illustrated in FIG. 4.
A) Construction of pAd D26 SV(A) No. 3(N) and rendering the Eco RI cleavage site blunt end Firstly, pAd D26 SV(A) No. 3 [acquired from Dr. Hiroshi Handa in Tokyo University; known by the thesis in Mol. Cell. Biol., 2(11), (1982)] DNA is cleaved with restriction enzyme Bgl II (manufactured by Boehringer Mannheim-Yamanouchi Co., Ltd.) in a conventional manner. Next, the DNA is rendered blunt end in a conventional manner using Klenow enzyme (manufactured by Boehringer Mannheim-Yamanouchi Co., Ltd.). After phenol treatment, enthanol precipitation and drying under reduced pressure, the precipitates are dissolved in distilled sterile water. After further performing ligation using the DNA ligation kit described above, E. coli HB101 competent cells (manufactured by Takara Shuzo Co., Ltd.) are transformed. Plasmid DNAs are acquired from transformants showing tetracycline resistance in a conventional manner.

After cleaving a part of these DNAs with restriction enzyme Bgl II, 0.7% agarose gel electrophoresis is performed. As the result, clone bearing DNA that is not cleaved with Bgl II is obtained. After digesting [pAd D26 SV(A) No. 3(N) plasmid] DNA of this clone with restriction enzyme Eco RI in a conventional manner, the DNA is made blunt end with Klenow enzyme as described above. After phenol treatment, enthanol precipitation and drying under reduced pressure, the precipitates are dissolved in distilled sterile water.

B) Isolation of Kpn I-Bam HI (about 2,900 base pairs) from pKSV 10 and rendering blunt end After cleaving pKSV 10 (manufactured by Pharmacia Fine Chemicals) DNA with restriction enzymes Kpn I and Bam HI in a conventional manner, the DNA is rendered blunt end using T4 DNA polymerate (manufactured by Takara Shuzo Co., Ltd.) and Klenow enzyme (the Laboratory Manual, pages 114–121). Next, 0.7% agarose gel electrophoresis is performed to separate a fragment of about 2,900 base pairs. Then the fragment is subjected to electric elution to recover the DNA.

C) Construction of pVY1

After ligating the DNA fragment obtained in A) and the DNA fragment obtained in B) using the DNA ligation kit, E. coli HB101 competent cells (described above) is transformed with the ligated product.

From the transformants showing tetracycline resistance, plasmid DNAs are prepared in a conventional manner. After cleaving a part of these plasmid DNAs with restriction enzyme Pst I (manufactured by Boehringer Mannheim-Yamanouchi Co., Ltd.) in a conventional manner, 1.0% agarose gel electrophoresis is carried out. As the result, a clone (plasmid pVY1) showing bands of about 3,400 base pairs, about 3,200 base pairs and about 1,400 base pairs is obtained. This clone E. coli HB101/pVY1 has been deposited in the Fermentation Research Institute of the Agency of Industrial Science & Technology of Japan under Registration No. P-9625 (FERM BP 2106).

4-2) Integration of Improved t-PA [II] Gene into Vector pVY1

After cleaving the plasmid pVY1 DNA produced in Example 4-1) with restriction enzyme Bgl II in a conventional manner, dephosphorylation is performed using alkali phosphatase (manufactured by Takara Shuzo Co., Ltd.). Thereafter phenol treatment is carried out 3 times. After enthanol precipitation and drying under reduced pressure, the precipitates are dissolved in distilled sterile water.

After ligating this DNA with the Bgl II-Xho II fragment (about 1,500 base pairs) produced in Example 2-3) using the DNA ligation kit, E. coli HB101 competent cells are transformed with the ligation product according to the method described above. From the transformants showing tetracycline resistance, plasmid DNA's are acquired in a conventional manner. After cleaving these DNAs with restriction enzymes (Bgl II, Pst I), a clone having integrated the improved t-PA [II] gene into vector pVY1 in the desired direction is selected based on pattern analysis by agarose gel electrophoresis. Firstly a part of these DNAs are cleaved with restriction enzyme Bgl II and 0.8% agarose gel electrophoresis is then carried out to obtain a clone having a band of about 1,500 base pair fragment. When the Bgl II-Xho II fragment is ligated with the Bgl II fragment of pVY1, the ligated portion of Xho II and Bgl II can be cut off with restriction enzyme Bgl II.

A part of plasmid DNAs of these clones is further cleaved with restriction enzyme Pst I and the DNAs are subjected to 0.8% agarose gel electrophoresis to obtain a clone having one band at about 3,400 base pairs, two bands at about 2,300 base pairs, one band at about 1,400 base pairs, and one band at about 80 base pairs. Using this clone (plasmid pVY1-t-PA [II], plasmid DNAs are mass produced according to the Laboratory Manual described above, page 86.

EXAMPLE 5

Integration of Improved t-PA [V], [VI] and [VIII] Genes into Vector pVY1

After plasmid pVY1 DNA prepared in Example 4-1) is cleaved with restriction enzyme Bgl II in a conventional manner, dephosphorylation is performed using alkaline phosphatase (manufactured by Takara Shuzo Co., Ltd.), treatment with phenol 3 times, ethanol precipitation and drying under reduced pressure follow. The residue is then dissolved in sterile distilled water.

After this DNA is ligated with the Bgl II-Xho II fragment (about 1,500 base pairs) prepared in Examples 2, 2-3) using the DNA ligation kit, the ligation product is transformed on the aforesaid *E. coli* HB101 competent cells. Plasmid DNAs are acquired from transformants showing tetracycline resistance in a conventional manner. After cleaving these DNAs with restriction enzymes (Bgl II, Pst I), agarose gel electrophoresis is performed. By analysis of the agarose gel electrophoresis pattern, clones in which the improved t-PA [V] gene is incorporated into vector pVY1 in the desired direction are selected. Firstly, after cleaving a part of these DNAs with restriction enzyme Bgl II, electrophoresis is carried out in a concentration of 0.8% agarose gel to give clones showing a band of the fragment of about 1,500 base pairs. When the Bgl II-Xho II fragment is bound to the Bgl II fragment of pVY1, the bound Xho II and Bgl II portion can be cleaved by restriction enzyme Bgl II due to the aforesaid isoshizomer configuration.

After further cleaving a part of plasmid DNAs of these clones with restriction enzyme Pst I, electrophoresis is carried out in a concentration of 0.8% agarose gel to give a clone showing one band at about 3,400 base pairs, one at about 2,300 base pairs, 2 bands at about 1,400 base pairs, one band at about 800 base pair and one band at about 80 base pair. Using the clone (plasmid pVY1-t-PA [V]), plasmid DNA is produced in large quantities based on the Laboratory Manual at page 86 described above.

In a similar manner, improved t-PA [VI] and [VIII] genes are integrated into vector pVY1.

EXAMPLE 6

Expression of Improved t-PA in CHO Cells

Plasmid pVY1-improved t-PA [VI] gene (t-PA [II], t-PA [V], t-PA [VI] or t-PA [VIII]) is transfected in DHFR-deficient CHO cells [Urlaub, et al., Proc. Natl. Acad. Sci. USA, 77(7), 4216–4220 (1980)] by the calcium phosphate method [Graham, et al., Virology, 52, 456 (1973)]. It is found that the transformant clone obtained from selection medium [MEM ALPHA (−), GIBCO] in the presence of methotrexate (MTX) produces t-PA activity of 50 to 100 U/ml (value determined by fibrin/agarose plate method, later described). This clone is used for subsequent studies. As production medium, GIT medium (manufactured by Wako Pure Chemical Industry Co., Ltd.) is used and 20 KIU/ml [SIGMA] of aprotinin is supplemented.

EXAMPLE 7

Purification of Improved t-PA from the Culture Supernatant of CHO Cells

The culture supernatant obtained in Example 6 is partially purified through anti-t-PA monoclonal antibody affinity column. Monoclonal antibody-producing hybridoma is produced to human melanoma cell-derived t-PA in a conventional manner. The antibody-producing hybridoma is inoculated to mice and monoclonal antibody (subclass: IgG1) developed in the ascites is recovered and purified using Protein A Cellulofine (manufactured by Biochemical Industry Co., Ltd.) and MAPS buffer system for purifying monoclonal antibody manufactured by Biorad Laboratories. The antibody is coupled to CNBr-activated Sepharose (manufactured by Pharmacia Fine Chemicals) in a ratio of 4 mg per 1 ml of the gel in a conventional manner.

The antibody gel, 24 ml, is mixed with 4 liters of the culture supernatant. After gently shaking overnight at 4° C., the gel is packed in a column (diamter of 1.5 cm×20 cm). Next, the gel is sequentially washed with 125 ml each of ① Tris-hydrochloride buffer, pH 7.4 (buffer A) containing 25 KIU/ml of aprotinin (manufactured by SIGMA) and 0.01% (w/v) of Tween 80, ② buffer A containing 0.5M NaCl, ③ buffer A containing 4M of urea and ④ buffer A. The improved t-PA bound to the gel is eluted with 0.2M glycine-hydrochloride buffer, pH 2.5 (containing 25 KIU/ml of aprotinin and 0.01% (w/v) of Tween 80). The active fractions are recovered and combined. After dialyzing to 10 mM Tris-hydrochloride buffer, pH 7.4 (containing 25 KIU/ml of aprotinin and 0.01% (w/v) of Tween 80) overnight, the dialysate is concentrated to 20- to 30-fold with a vacuum centrifuging concentrater (Speed VAC, manufactured by SAVANT Inc.). The concentrate is again dialyzed to 10 mM Tris-hydrochloride buffer, pH 7.4 (containing 0.15M NaCl, 25 KIU/ml of aprotinin and 0.01% (w/v) of Tween 80) overnight and used for subsequent evaluation in vitro and in vivo. Finally, the specific activity is increased by 3,700 to 5,000 times and 36 to 42% t-PA activity (determined by fibrin/agarose plate method) is recovered.

This active fraction is analyzed by SDS-electrophoresis and silver staining. Under the reducing condition, a very strong band is noted around 54 killodaltons, together with other several bands. Furthermore the gel after the electrophoresis is treated with 2.5% (w/v) Triton X-100 and then put on fibrin/agarose plate to perform fibrin autography at 37° C., whereby a dissolved band is noted at about 50 killodaltons. On the same plate, naturally occurring t-PA appears at about 60 killodaltons. The results strongly suggest that t-PA adsorbed to the antibody affinity column and eluted by the procedure would be the improved t-PA having a molecular weight theoretically smaller by 10,000 than that of naturally occurring type.

EXAMPLE 8

Measurement of Specific Activity of Improved t-PA

The protein amount of the partially purified improved t-PA is determined by measuring the total protein according to the method of Bradford [Bradford, Anal. Biochem., 72, 248 (1976)] using bovine serum albumin as standard protein. The amount of t-PA antigen is measured by ELISA. ELISA is sandwich type using the monoclonal antibody used for the antibody column described above and biotinated rabbit anti-t-PA antibody (manufactured by American Diagnostica Inc.) and a color is formed using biotinated horse raddish peroxidase streptavidin complex (manufactured by Amersham Co., Ltd.) and its substrate (3,3',5,5'-tetramethylbentidine). As standard t-PA, human melanoma cell-derived single stranded t-PA manufactured by American Diagnositca Inc. is used.

Fibrinolytic activity is determined by the fibrin/agarose plate method and the $^{125}$I-labeled fibrin film dissolution method. The fibrin/agarose plate is prepared by adding agar to 95% coagulated fibrinogen. The $^{125}$I-labeled fibrin film dissolution method is performed according to the method of Hoyraerts et al. [J. Biol. Chem., 257, 2912 (1982)]. That is, a suitable amount of $^{125}$I-labeled fibrinogen (manufactured by ICN Biomedical Co., Ltd.) is added to 1.8 μM fibrinogen and the mixture is charged in a 96 well microtiter plate (manufactured by Limbro Co., Ltd.) by 50 μl each/well followed by drying at 400C overnight. Then 100 μl each of 1.6 U/ml of thrombin (manufactured by Mochida Pharmaceutical Co., Ltd.) is added. The mixture is allowed to stand at 37° C. for 4 hours to fibrinate. After washing twice with 10 mM phosphate buffer containing 0.2% calf serum albumin and 0.9% NaCl, the plate is provided for determination of the activity. In each well 50 μl of 200 nM plasminogen is charged and further 50 μl of t-PA standard or improved t-PA is added thereto. After mixing them, the mixture is reacted at 37° C. for 2 hours. From each well 50 μl is taken and the dissolved $^{125}$I-fibrin is measured with Auto Well Gamma Counter manufactured by Aloka Inc. and by comparing with the standard curve prepared using standard t-PA, the fibrinolytic activity of improved t-PA is calculated. The standard t-PA used is human melanoma cell-derived t-PA manufactured by Bioscott Inc. standardized according to International t-PA Standard [Gaffuey and Curtis, Thromb. Haemostas., 53, 134 (1985)].

The specific activity value calculated from the activity value determined by the $^{125}$I-fibrin film method and the antigen amount determined by ELISA is 300,000 to 420,000 U/mg antigen.

EXAMPLE 9

Affinity of Improved t-PA to Fibrin and Activation with Fibrin

According to Verheijen, et al. [[EMBO J., 5, 3525 (1986)], affinity of improved t-PA to fibrin is examined. To fibrinogen in various concentrations, improved or naturally occurring t-PA (1,000 U/ml) is added and 1 U of thrombin is further added thereto followed by reacting at room temperature for 3 minutes. The formed fibrin clot is precipitated by centrifugation at 16,000 r.p.m. for 8 mins. and the amount of t-PA which is not bound to fibrin in the supernatant is determined by activity measurement by the fibrin/agarose plate method. As the result, improved t-PA [VI] shows an equal affinity to fibrin, as compared to natural type. In order to examine a plasminogen activation rate of the improved t-PA in the presence or absence of fibrin, the following run is carried out. Using a 96 well microtiter plate, naturally occurring or improved t-PA is added to 0.1M Tris-hydrochloride buffer, pH 7.5, containing 0.3 mM synthetic p-nitroanilide-tripeptide synthetic substrate S-2251 (H-D-Val-Leu-Lys-pNA.HCl, manufactured by Kabi Inc.), 0.13 μM plasmin-free plasminogen, 120 μg/ml of DESAFIB™ (manufactured by American Diagnostica Inc.) and 0.1% Tween 80 to make the whole volume 200 μl. The system is kept at 37° C. After a definite time period, absorbency (A 405 nm) at wavelength of 405 nm is measured with Titertech Multiscan Model 310.

Figure 9:
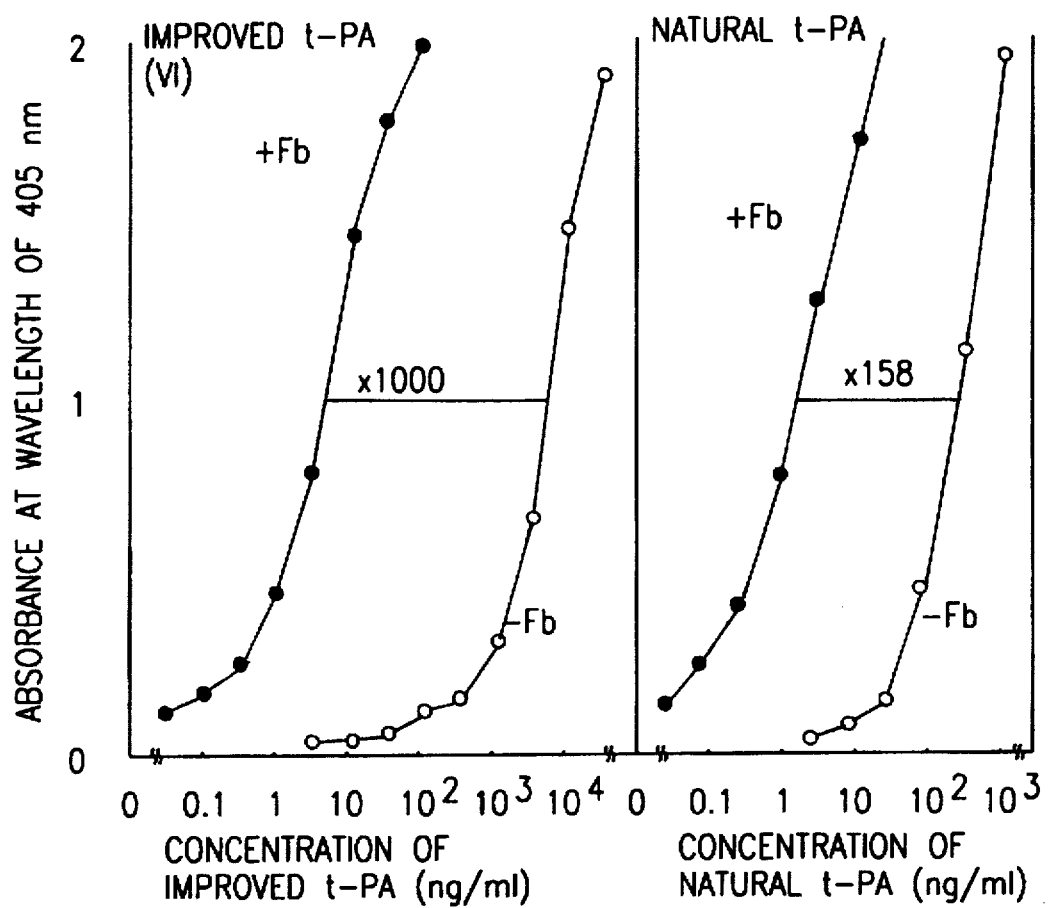
FIG. 9 shows the dose-response curve of the t-PA activity of improved t-PA [VI] and naturally occurring t-PA by the S-2251 method in the presence (+Fb) and absence (−Fb) of a fibrin substitute.

Th dose-response curve of improved t-PA [VI] and naturally occurring t-PA in amidolytic activity is shown in FIG. 9. When the activation rate is compared by shift of the dose-response curve due to the addition of DESAFIB™, naturally occurring t-PA is 158 times whereas improved t-PA [VI] reaches 1000 times. This is due to the fact that the activity of improved t-PA [VI] in the absence of DESAFIB™ is lower by about 1/20 than that of natural t-PA.

EXAMPLE 10

Analysis of Improved t-PA on Fibrinolytic Activity in Rabbit Blood Flow

Figure 10:
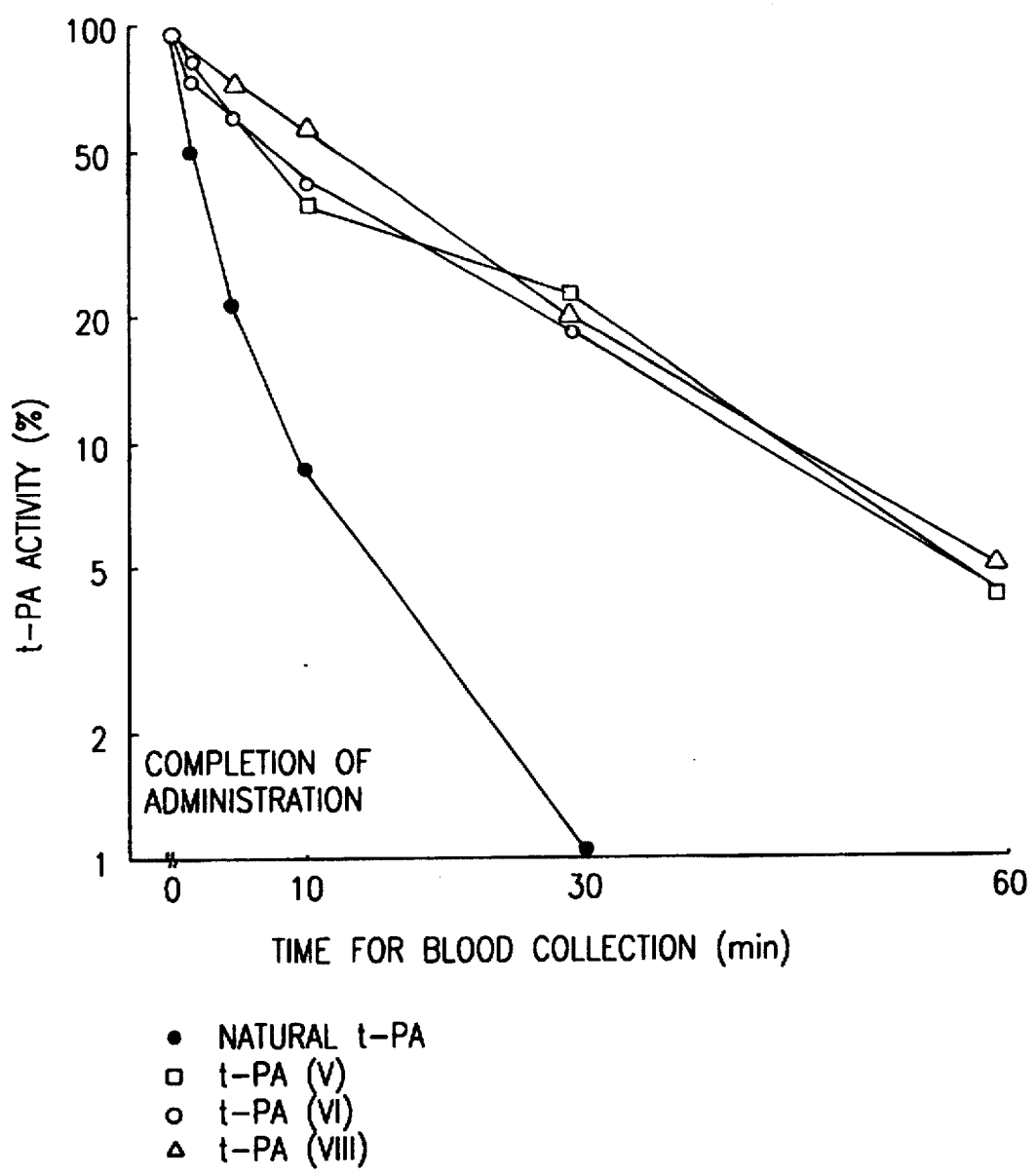
FIG. 10 shows change in activity of improved t-PA [VI] and naturally occurring t-PA in rabbit blood with passage of time.

Pharmacokinetic is examined in view of the activities of naturally occurring t-PA (n-t-PA) and the improved t-PA of the present invention in rabbit. As is clear from FIG. 10, the improved t-PA shows remarkable prolongation of the half life in the activity value. More specifically, natural t-PA shows the half life for 1 to 2 minutes, whereas that of the improved t-PA shows 8 to 15 minutes. In addition, it is noted that the activity value of 5% (the value 30 seconds after the administration is made 100%) still remains in the improved t-PA even 60 minutes after the administration. On the other hand, natural t-PA shows the activity value of 0.1% 60 minutes after.

This experiment is carried out as follows.

For the run, Japanese white rabbit weighing 2.4 kg is used. Under pentobarbital anesthesia, t-PA is administered through the peripheral vein of the ear. The dose is 15,400 U/0.8 ml/rabbit of improved t-PA and 5,400 U/0.8 ml/rabbit of n-t-PA (value determined by the fibrin plate method). Subsequently, 2.5 ml each of blood is collected from the femoral artery using a catheter in various time intervals (0.5 to 60 minutes) and taken in 1/9 volume of sodium citrate (3.8%). Within 30 minutes after blood collection, centrifugation is performed at a low speed to separate plasma. Using the separated plasma, the t-PA activity in blood is measured.

(1) Measurement of t-PA activity

After diluting 0.2 ml of plasma with 3 mM glacial acetic acid to 16-fold, the dilution is centrifuged at a low speed to give precipitates. The precipitates are dissolved in 20 mM Tris-HCl, pH 7.4–140 mM NaCl buffer of a volume equivalent to the plasma to obtain euglobulin fraction. The t-PA activity is determined by adding this euglobulin fraction into fibrin/agarose plate. After incubation of the plate at 37° C. for 16 hours, the t-PA activity is observed as plaque. The fibrin/agarose plate is prepared as follows.

Commercially available fibrinogen (fraction I of corn) is used for preparation of fibrin/agarose plate as plasminogen-rich fibrinogen. The final concentration of plasminogen-rich fibrinogen is 1.5 mg/ml in 20 mM Tris-HCl buffer, pH 7.4, containing 130 mM NaCl and $10^{-4}$M $CaCl_2$. The final agarose concentration is 0.75% in the same buffer. Thrombin (40 NIH units/ml), 100 μl, is added to 10 ml of fibrinogen agarose solution to prepare a plate. The standard curve for the fibrin/agarose plate method is obtained by diluting t-PA used for administration to the animal to 0.1 to 10,000 U/ml. The thus determined t-PA activity in blood is expressed by per cent, using the t-PA activity obtained by collecting blood 30 seconds after the administration as 100%.

EXAMPLE 11

Stability of Improved t-PA [VI] to Heat and Acids

Figure 11:
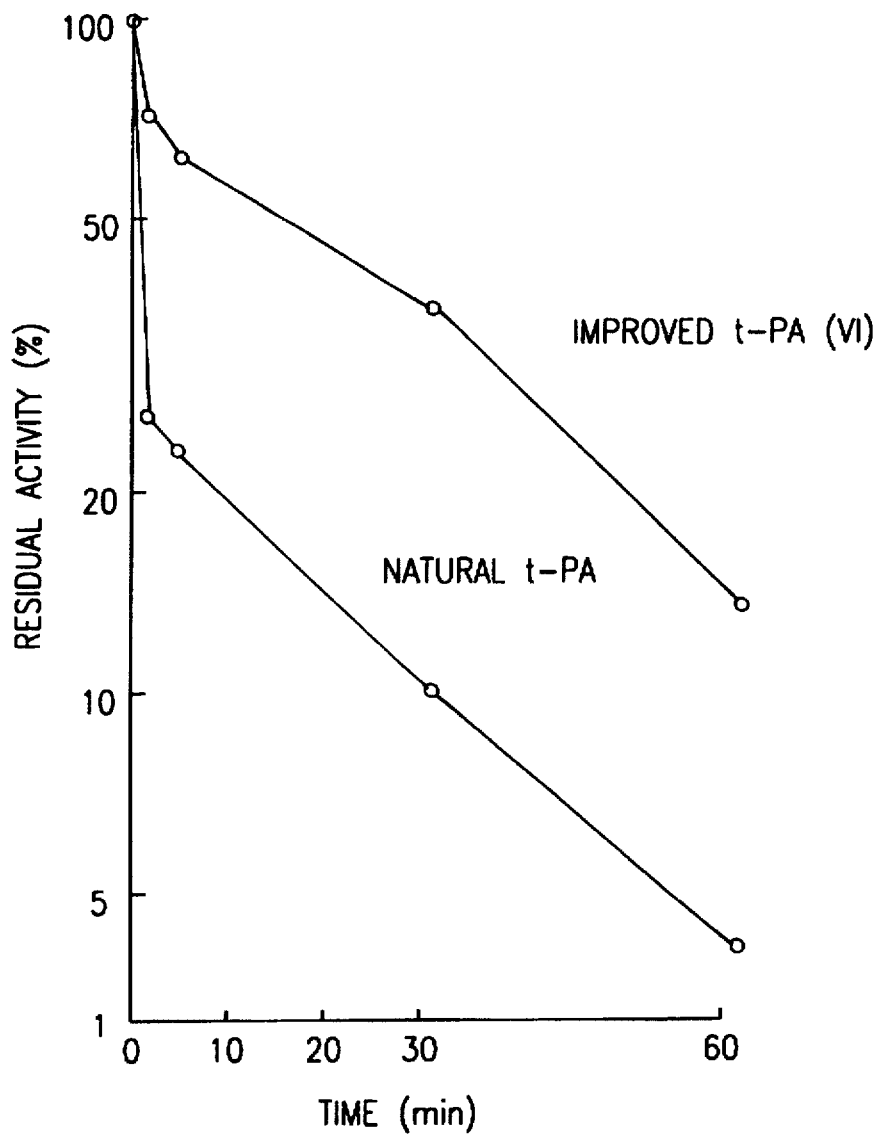
FIG. 11 shows change in residual activity of improved t-PA [VI] after heat treatment.

Stability of improved t-PA [VI] is examined. With respect to stability to heat, improved t-PA [VI] and natural t-PA are diluted with 50 mM Tris buffer (containing 100 mM NaCl and 0.01% Tween 80), pH 7.4, to a concentration of 100 μg/ml, respectively. Each solution is allowed to stand in boiling water (98° C.) for 2 to 60 minutes. After cooling, the remaining activity is determined by the fibrin plate method. As shown in FIG. 11, reduction in the activity of improved t-PA [VI] is very gentle as compared to that of natural t-PA. For example after heat treatment for 2 minutes, the activity of natural t-PA is reduced to 25%, whereas in improved t-PA [VI], the activity of 71% still remains.

Improved t-PA [VI] and natural t-PA are dissolved in 0.5N hydrochloric acid in a concentration of 100 μg/ml followed by allowing to stand at room temperature for 30 minutes. After neutralization, the activity is determined by the fibrin plate method. In the improved t-PA, no activity changes at all, whereas in natural t-PA, the activity is reduced by 50%.

EXAMPLE 12

Inhibition of LAF Activity with Improved t-PA [VI]

Improved t-PA [VI] and natural t-PA are suitably diluted with tissue culture medium RPMI 1640 containing 7% calf fetal serum and 58 µM 2-mercaptoethanol. This dilution, 100 µl, is charged in a 96 well flat bottomed multiplate and, 50 µl each of cell suspension containing thymocyte ($2 \times 10^7$ cells/ml) collected from male C3H/HeJ mice of 4 to 6 weeks age and Concanavalin A (1.2 µg/ml) and 50 µl of IL-1 (4 units/ml, Genzyme Inc.) are added followed by culturing for 48 hours in an incubator at 37° C. containing 5% carbon dioxide. Then, $^3$H-thymidine is added in 0.5 µCi/20 µl/well. After culturing for further 18 hours, the cells are gathered on a glass fiber filter using a cell harvester and the amount of $^3$H-thymidine incorporated into the cells is measured with a liquid scintillation counter thereby to determine the LAF activity.

Figure 12:
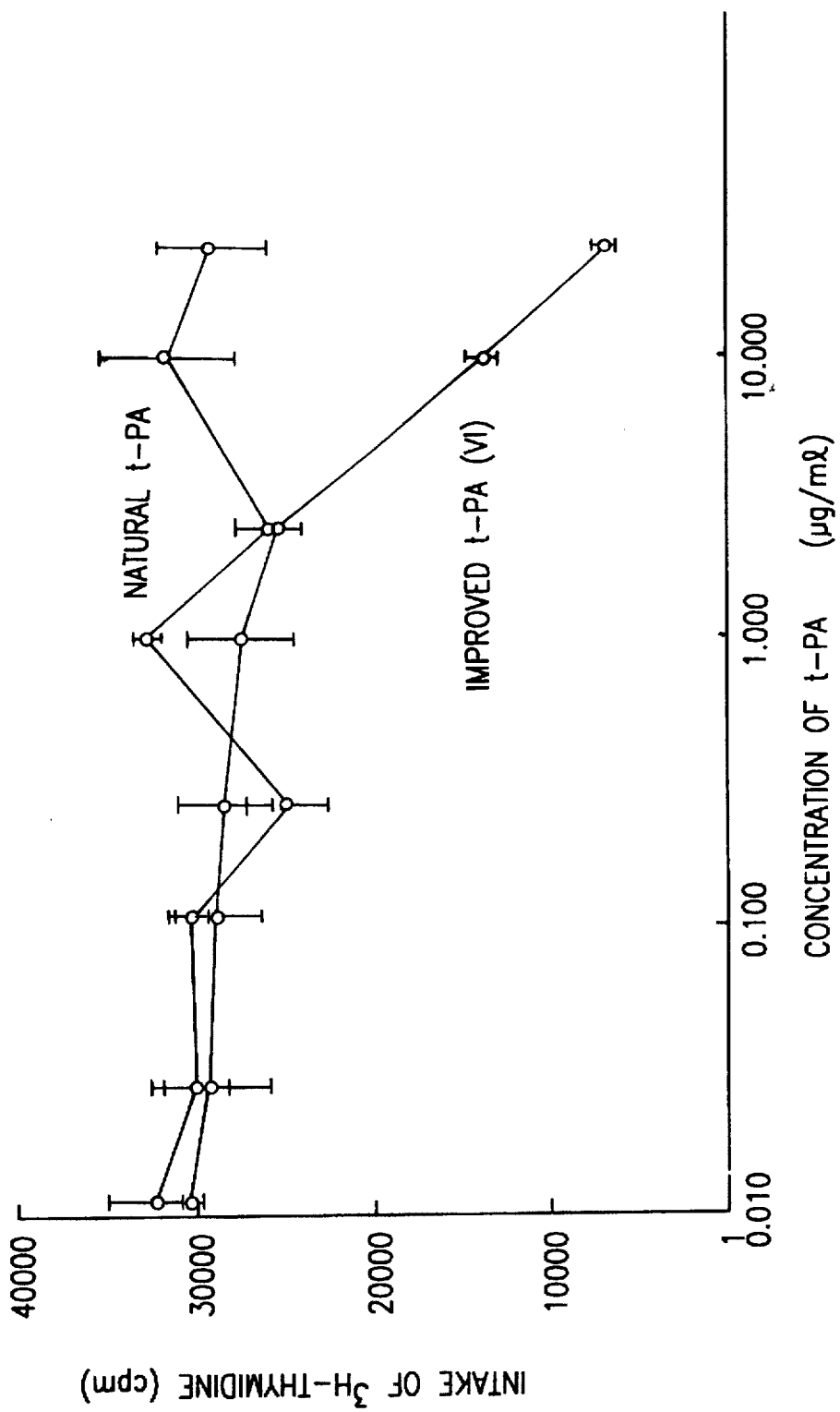
FIG. 12 shows inhibition of improved t-PA [VI] against LAF activity.

As shown in FIG. 12, natural t-PA does not inhibit the LAF activity at all but the improved t-PA significantly inhibits the LAF activity by IL-1. When tested with the solvent alone, no influence is noted.

EXAMPLE 13

Antiinflammatory Activity Based on the Action on Denatured Protein

1) Preparation of denatured protein

After a protein solution (5 mg/ml) is incubated in 0.1N HCl or 0.1N NaOH at 37° C. for 2 to 3 hours, the protein solution is neutralized with the same amount of NaOH or HCl to prepare the denatured protein.

2) Affinity of improved t-PA [VI] to denatured protein
Method:

According to the procedure shown below, denatured protein is adhered to a piece of nitrocellulose film. Next, the amount of improved t-PA bound to the piece of nitrocellulose film is measured, whereby the affinity of the improved t-PA to denatured protein is determined.

A piece of nitrocellulose film is charged into 20 mM Tris-hydrochloride buffer, pH 7.5 (TBS buffer) containing 140 mM NaCl

drying

Denatured protein (50 µg/10 µl) is dropped onto the piece of nitrocellulose film

drying

Blocking with 3% gelatin solution

washing

The piece of nitrocellulose film is charged in 1 µg of improved t-PA/ml.

washing

Plasminogen and synthetic substrate S-2251 are added followed by incubation at 37° C. (quantitative assay for the improved t-PA adsorbed)

↓

Measurement of OD 405

Results:
As shown in the following table, the improved t-PA shows affinity to IgG treated with HCl and to the albumin treated with HCl and to the albumin treated with NaOH. On the other-hand, the improved t-PA does not show affinity to intact IgG and albumin.

| Kind of protein adhered to cellulose film | Amount of improved t-PA bound (ng/piece of cellulose film) |
|---|---|
| Buffer | 0 |
| IgG | 0.2 |
| HCl-treated IgG | 1.35 |
| Albumin | 0 |
| NaOH-treated albumin | 0.9 |

3) Activation of improved t-PA [VI] with denatured protein
Method:

Plasminogen (Kabi Inc.), 0.0078 CU/10 µl, 100 µl of 3 mM synthetic substrate S-2251 and various amounts of TBS buffer are added to the reaction solution of improved t-PA activator (denatured protein or BrCN-treated fibrinogen or the like) in various concentrations to make the amount of reaction solution 0.275 ml. The improved t-PA, 2.5 ng/25 µl, is added to the reaction solution to initiate the reaction. After reacting for a definite time period, 2% SDS solution is added in an equimolar amount to the reaction solution to discontinue the reaction. By measuring OD 405, the activity of improved t-PA is determined.

Results:
As shown in FIG. 13, NaOH-treated albumin and HCl-treated IgG exhibit a potent activation of the improved t-PA. Particularly in the HCl-treated IgG, the activation is strong and the activity of the HCl-treated IgG is substantially identical with that of the BrCN-treated fibrinogen in a concentration smaller by one-several tenths time than in the BrCN-treated fibrinogen. However, the intact albumin and IgG shows no activation.

4) Degradation of denatured protein with improved t-PA [VI]
Method:

After reacting the denatured protein with the improved t-PA under the same conditions as the method described in "3) Activation of improved t-PA with denatured protein" except for adding no synthetic substrate S-2251 to the reaction system and fixing the amount of denatured protein to 133 µg/ml, SDS gel electrophoresis is performed in the presence of β-mercaptoethanol.

Figure 14:
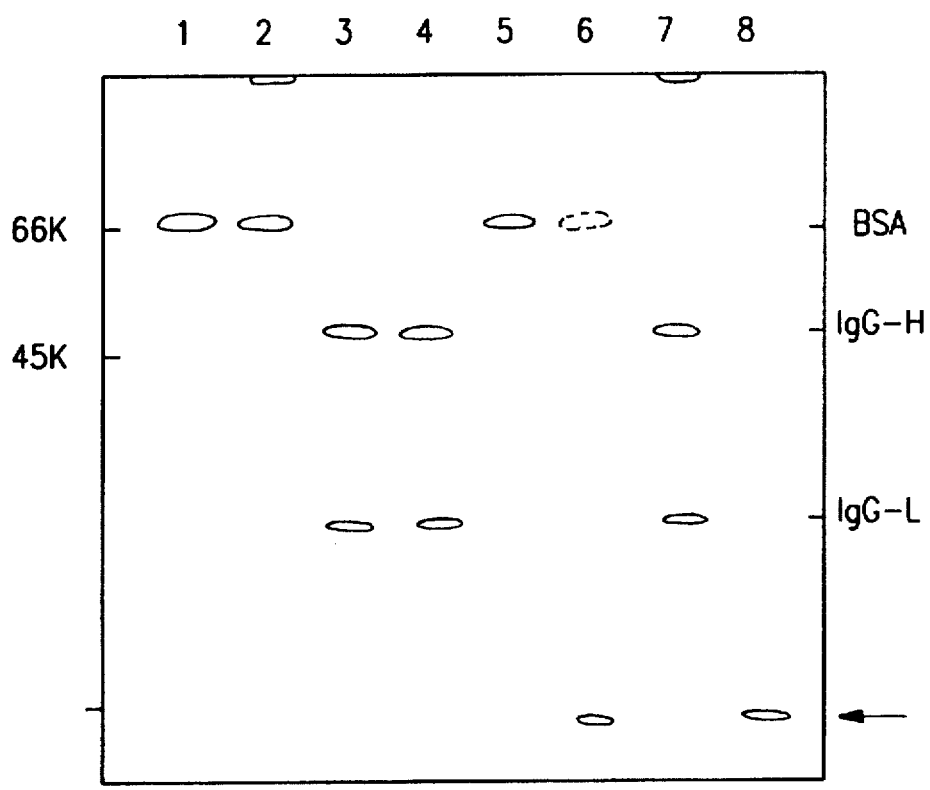
FIG. 14 shows degradation of denatured protein with improved t-PA [VI].

Results:
As shown in FIG. 14, the protein denatured by NaOH treatment or HCl treatment causes disappearance of bands and formation of degradation products, indicating decomposition of the denatured protein. On the other hand, with the intact albumin, no change is noted in band even after reacting with the improved t-PA and therefore, no degradation of the denatured protein is noted.

We claim:
1. An improved tissue plasminogen activator gene represented by the following base sequence:

5'ATGGATGCAATGAAGAGAGGGCTGCGT
GTGCTGCTACTCTGCGGAGCAGTCTTCGTT
TCGCCCAGCCAGGAAATCCATGCCCGATTC
AGAAGAGGAGCCAGGTCTTACCAAGTGATC
TGCAGAGATGAAAAACGCAGATGATATAC
CAGCAACATCAGTCATGGCTGCGCCCTGTG
CTCAGAAGCAACCGGGTGGAATATTGCTGG
TGCAACAGTGGCAGGGCACAGTGCCACTCA
GTGCCTGTCAAAAGTTGCAGCGAGCCAAGG
TGTTTCAACGGGGGCACCTGCCAGCAAGCT
TTGTACTTCTCAGATTTCGTGTGCCAGTGC
CCCGAAGGATTTGCTGGGAAGTGCTGTGAA
ATAGATACTCGAGCCACGTCTGAGGGAAAC
AGTGACTGCTACTTTGGGAATGGGTCAGCC
TACCGTGGTACCCACAGCCTCACCGAGTCG
GGTGCCTCCTGCCTCCCATGGAATTCCATG
ATCCTGATAGGCAAGGTTTACACAGCACAG
AACCCAGTGCCCAGGCACTGGGCCTGGGC
AAACATAATTACTGCCGGAATCCTGATGGG
GATGCCAAGCCCTGGTGCCACGTGCTGAAG
AACCGCAGGCTGACGTGGGAGTACTGTGAT
GTGCCCTCCTGCTCCACCTGCGGCCTGAGA
CAGTACAGCCAGCCTCAGTTTGAAATCAAA
GGAGGGCTCTTCGCCGACATCGCCTCCCAC
CCCTGGCAGGCTGCCATCTTTGCCAGCAC
AGGAGGTCGCCCGGAGAGCGGTTCCTGTGC
GGGGGCATACTCATCAGCTCCTGCTGGATT
CTCTCTGCCGCCCACTGCTTCCAGGAGAGG
TTTCCGCCCCACCACCTGACGGTGATCTTG
GGCAGAACATACCGGGTGGTCCCTGGCGAG
GAGGAGCAGAAATTTGAAGTCGAAAAATAC
ATTGTCCATAAGGAATTCGATGATGACACT
TACGACAATGACATTGCGCTGCTGCAGCTG
AAATCGGATTCGTCCCGCTGTGCCCAGGAG
AGCAGCGTGGTCCGCACTGTGTGCCTTCCC
CCGGCGGACCTGCAGCTGCCGGACTGGACG
GAGTGTGAGCTCTCCGGCTACGGCAAGCAT
GAGGCCTTGTCTCCTTTCTATTCGGAGCGG
CTGAAGGAGGCTCATGTCAGACTGTACCCA
TCCAGCCGCTGCACATCACAACATTTACTT
AACAGAACAGTCACCGACAACATGCTGTGT
GCTGGAGACACTCGGAGCGGCGGGCCCCAG
GCAAACTTGCACGACGCCTGCCAGGGCGAT
TCGGGAGGCCCCCTGGTGTGTCTGAACGAT
GGCCGCATGACTTTGGTGGGCATCATCAGC
TGGGGCCTGGGCTGTGGACAGAAGGATGTC
CCGGGTGTGTACACCAAGGTTACCAACTAC
CTAGACTGGATTCGTGACAACATGCGACCG
TGA3' wherein A is deoxyadenyl, G is deoxyguanyl, C is deoxycytidyl and T is deoxythymidyl.

2. An improved tissue plasminogen activator gene coding for the following amino acid sequence:

| H$_2$N—R— | Ser | Tyr | Gln | Val | Ile | Cys | Arg | Asp | Glu | Lys |
|---|---|---|---|---|---|---|---|---|---|---|
| | Thr | Gln | Met | Ile | Tyr | Gln | Gln | His | Gln | Ser |
| | Trp | Leu | Arg | Pro | Val | Leu | Arg | Ser | Asn | Arg |
| | Val | Glu | Tyr | Cys | Trp | Cys | Asn | Ser | Gly | Arg |
| | Ala | Gln | Cys | His | Ser | Val | Pro | Val | Lys | Ser |
| | Cys | Ser | Glu | Pro | Arg | Cys | Phe | Asn | Gly | Gly |
| | Thr | Cys | Gln | Gln | Ala | Leu | Tyr | Phe | Ser | Asp |
| | Phe | Val | Cys | Gln | Cys | Pro | Glu | Gly | Phe | Ala |
| | Gly | Lys | Cys | Cys | Glu | Ile | Asp | Thr | Arg | Ala |
| | Thr | Ser | Glu | Gly | Asn | Ser | Asp | Cys | Tyr | Phe |
| | Gly | Asn | Gly | Ser | Ala | Tyr | Arg | Gly | Thr | His |
| | Ser | Leu | Thr | Glu | Ser | Gly | Ala | Ser | Cys | Leu |
| | Pro | Trp | Asn | Ser | Met | Ile | Leu | Ile | Gly | Lys |
| | Val | Tyr | Thr | Ala | Gln | Asn | Pro | Ser | Ala | Gln |
| | Ala | Leu | Gly | Leu | Gly | Lys | His | Asn | Tyr | Cys |
| | Arg | Asn | Pro | Asp | Gly | Asp | Ala | Lys | Pro | Trp |

-continued

|     |     |     |     |     |     |     |     |     |     |
| --- | --- | --- | --- | --- | --- | --- | --- | --- | --- |
| Cys | His | Val | Leu | Lys | Asn | Arg | Arg | Leu | Thr |
| Trp | Glu | Tyr | Cys | Asp | Val | Pro | Ser | Cys | Ser |
| Thr | Cys | Gly | Leu | Arg | Gln | Tyr | Ser | Gln | Pro |
| Gln | Phe | —   | Y   | —   | Gly | Gly | Leu | Phe | Ala |
| Asp | Ile | Ala | Ser | His | Pro | Trp | Gln | Ala | Ala |
| Ile | Phe | Ala | Lys | His | Arg | Arg | Ser | Pro | Gly |
| Glu | Arg | Phe | Leu | Cys | Gly | Gly | Ile | Leu | Ile |
| Ser | Ser | Cys | Trp | Ile | Leu | Ser | Ala | Ala | His |
| Cys | Phe | Gln | Glu | Arg | Phe | Pro | Pro | His | His |
| Leu | Thr | Val | Ile | Leu | Gly | Arg | Thr | Tyr | Arg |
| Val | Val | Pro | Gly | Glu | Glu | Glu | Gln | Lys | Phe |
| Glu | Val | Glu | Lys | Tyr | Ile | Val | His | Lys | Glu |
| Phe | Asp | Asp | Asp | Thr | Tyr | Asp | Asn | Asp | Ile |
| Ala | Leu | Leu | Gln | Leu | Lys | Ser | Asp | Ser | Ser |
| Arg | Cys | Ala | Gln | Glu | Ser | Ser | Val | Val | Arg |
| Thr | Val | Cys | Leu | Pro | Pro | Ala | Asp | Leu | Gln |
| Leu | Pro | Asp | Trp | Thr | Glu | Cys | Glu | Leu | Ser |
| Gly | Tyr | Gly | Lys | His | Glu | Ala | Leu | Ser | Pro |
| Phe | Tyr | Ser | Glu | Arg | Leu | Lys | Glu | Ala | His |
| Val | Arg | Leu | Tyr | Pro | Ser | Ser | Arg | Cys | Thr |
| Ser | Gln | His | Leu | Leu | Asn | Arg | Thr | Val | Thr |
| Asp | Asn | Met | Leu | Cys | Ala | Gly | Asp | Thr | Arg |
| Ser | Gly | Gly | Pro | Gln | Ala | Asn | Leu | His | Asp |
| Ala | Cys | Gln | Gly | Asp | Ser | Gly | Gly | Pro | Leu |
| Val | Cys | Leu | Asn | Asp | Gly | Arg | Met | Thr | Leu |
| Val | Gly | Ile | Ile | Ser | Trp | Gly | Leu | Gly | Cys |
| Gly | Gln | Lys | Asp | Val | Pro | Gly | Val | Tyr | Thr |
| Lys | Val | Thr | Asn | Tyr | Leu | Asp | Trp | Ile | Arg |
| Asp | Asn | Met | Arg | Pro—COOH | | | | | |

Wherein Y represents Glu-Ile-Lys; COOH represents the carboxy terminal; and R is a single bond or represents:

|     |     |     |     |     |     |     |     |     |     |
| --- | --- | --- | --- | --- | --- | --- | --- | --- | --- |
| Met | Asp | Ala | Met | Lys | Arg | Gly | Leu | Cys | Cys |
| Val | Leu | Leu | Leu | Cys | Gly | Ala | Val | Phe | Val |
| Ser | Pro | Ser | Gln | Glu | Ile | His | Ala | Arg | Phe |
| Arg | Arg | Gly | Ala | Arg, | | | | | |
| Gly | Ala | Arg, | | | | | | | |
| Met, | | | | | | | | | | or,

|     |     |     |     |
| --- | --- | --- | --- |
| Met | Gly | Ala | Arg. |

3. A host cell transformed with the gene of claim 2.

4. A process for preparing a novel tissue plasminogen activator having the following amino acid sequence in which, compared to human t-PA, kringle 1 is deleted and Arg 275 is substituted by Glu:

| H$_2$N—R— | Ser | Tyr | Gln | Val | Ile | Cys | Arg | Asp | Glu | Lys |
| --- | --- | --- | --- | --- | --- | --- | --- | --- | --- | --- |
|     | Thr | Gln | Met | Ile | Tyr | Gln | Gln | His | Gln | Ser |
|     | Trp | Leu | Arg | Pro | Val | Leu | Arg | Ser | Asn | Arg |
|     | Val | Glu | Tyr | Cys | Trp | Cys | Asn | Ser | Gly | Arg |
|     | Ala | Gln | Cys | His | Ser | Val | Pro | Val | Lys | Ser |
|     | Cys | Ser | Glu | Pro | Arg | Cys | Phe | Asn | Gly | Gly |
|     | Thr | Cys | Gln | Gln | Ala | Leu | Tyr | Phe | Ser | Asp |
|     | Phe | Val | Cys | Gln | Cys | Pro | Glu | Gly | Phe | Ala |
|     | Gly | Lys | Cys | Cys | Glu | Ile | Asp | Thr | Arg | Ala |
|     | Thr | Ser | Glu | Gly | Asn | Ser | Asp | Cys | Tyr | Phe |
|     | Gly | Asn | Gly | Ser | Ala | Tyr | Arg | Gly | Thr | His |
|     | Ser | Leu | Thr | Glu | Ser | Gly | Ala | Ser | Cys | Leu |
|     | Pro | Trp | Asn | Ser | Met | Ile | Leu | Ile | Gly | Lys |
|     | Val | Tyr | Thr | Ala | Gln | Asn | Pro | Ser | Ala | Gln |
|     | Ala | Leu | Gly | Leu | Gly | Lys | His | Asn | Tyr | Cys |
|     | Arg | Asn | Pro | Asp | Gly | Asp | Ala | Lys | Pro | Trp |
|     | Cys | His | Val | Leu | Lys | Asn | Arg | Arg | Leu | Thr |
|     | Trp | Glu | Tyr | Cys | Asp | Val | Pro | Ser | Cys | Ser |
|     | Thr | Cys | Gly | Leu | Arg | Gln | Tyr | Ser | Gln | Pro |
|     | Gln | Phe | —   | Y   | —   | Gly | Gly | Leu | Phe | Ala |
|     | Asp | Ile | Ala | Ser | His | Pro | Trp | Gln | Ala | Ala |
|     | Ile | Phe | Ala | Lys | His | Arg | Arg | Ser | Pro | Gly |

-continued

| | | | | | | | | | |
|---|---|---|---|---|---|---|---|---|---|
| Glu | Arg | Phe | Leu | Cys | Gly | Gly | Ile | Leu | Ile |
| Ser | Ser | Cys | Trp | Ile | Leu | Ser | Ala | Ala | His |
| Cys | Phe | Gln | Glu | Arg | Phe | Pro | Pro | His | His |
| Leu | Thr | Val | Ile | Leu | Gly | Arg | Thr | Tyr | Arg |
| Val | Val | Pro | Gly | Glu | Glu | Glu | Gln | Lys | Phe |
| Glu | Val | Glu | Lys | Tyr | Ile | Val | His | Lys | Glu |
| Phe | Asp | Asp | Asp | Thr | Tyr | Asp | Asn | Asp | Ile |
| Ala | Leu | Leu | Gln | Leu | Lys | Ser | Asp | Ser | Ser |
| Arg | Cys | Ala | Gln | Glu | Ser | Ser | Val | Val | Arg |
| Thr | Val | Cys | Leu | Pro | Pro | Ala | Asp | Leu | Gln |
| Leu | Pro | Asp | Trp | Thr | Glu | Cys | Glu | Leu | Ser |
| Gly | Tyr | Gly | Lys | His | Glu | Ala | Leu | Ser | Pro |
| Phe | Tyr | Ser | Glu | Arg | Leu | Lys | Glu | Ala | His |
| Val | Arg | Leu | Tyr | Pro | Ser | Ser | Arg | Cys | Thr |
| Ser | Gln | His | Leu | Leu | Asn | Arg | Thr | Val | Thr |
| Asp | Asn | Met | Leu | Cys | Ala | Gly | Asp | Thr | Arg |
| Ser | Gly | Gly | Pro | Gln | Ala | Asn | Leu | His | Asp |
| Ala | Cys | Gln | Gly | Asp | Ser | Gly | Gly | Pro | Leu |
| Val | Cys | Leu | Asn | Asp | Gly | Arg | Met | Thr | Leu |
| Val | Gly | Ile | Ile | Ser | Trp | Gly | Leu | Gly | Cys |
| Gly | Gln | Lys | Asp | Val | Pro | Gly | Val | Tyr | Thr |
| Lys | Val | Thr | Asn | Tyr | Leu | Asp | Trp | Ile | Arg |
| Asp | Asn | Met | Arg | Pro—COOH | | | | | | wherein —Y— represents Glu Ile Lys, COOH represents the carboxy terminal and R is a single bond or represents:

| | | | | | | | | | |
|---|---|---|---|---|---|---|---|---|---|
| Met | Asp | Ala | Met | Lys | Arg | Gly | Leu | Cys | Cys |
| Val | Leu | Leu | Leu | Cys | Gly | Ala | Val | Phe | Val |
| Ser | Pro | Ser | Gln | Glu | Ile | His | Ala | Arg | Phe |
| Arg | Arg | Gly | Ala | Arg, | | | | | |
| Gly | Ala | Arg, | | | | | | | |
| Met, | | | | | | | | | | or,

| | | | |
|---|---|---|---|
| Met | Gly | Ala | Arg; | which comprises culturing the host cell of claim 3 and recovering the tissue plasminogen activator.

* * * * *